US006670887B2

(12) United States Patent
Dungan

(10) Patent No.: US 6,670,887 B2
(45) Date of Patent: Dec. 30, 2003

(54) APPARATUS AND METHOD FOR WIRELESS GAS MONITORING

(75) Inventor: Cornelius P. Dungan, Shaker Heights, OH (US)

(73) Assignee: Gastronics, Inc., Cleveland, OH (US)

( * ) Notice: Subject to any disclaimer, the term of this patent is extended or adjusted under 35 U.S.C. 154(b) by 351 days.

(21) Appl. No.: 09/854,748

(22) Filed: May 14, 2001

(65) Prior Publication Data

US 2001/0040509 A1 Nov. 15, 2001

Related U.S. Application Data

(63) Continuation-in-part of application No. 09/333,352, filed on Jun. 15, 1999, now Pat. No. 6,252,510.
(60) Provisional application No. 60/122,863, filed on Mar. 4, 1999, and provisional application No. 60/104,223, filed on Oct. 14, 1998.

(51) Int. Cl.[7] .............................................. G08B 17/10
(52) U.S. Cl. .................... 340/632; 340/633; 340/539.26
(58) Field of Search ................................ 340/501, 506, 340/509, 539.1, 539.26, 521, 522, 632, 633, 634; 73/23.2, 23.31, 31.02, 31.03

(56) References Cited

U.S. PATENT DOCUMENTS

| 4,464,651 A | * | 8/1984 | Duhame | ..................... 340/521 |
|---|---|---|---|---|
| 5,132,968 A | | 7/1992 | Cephus | ....................... 370/94.1 |
| 5,148,148 A | * | 9/1992 | Shima et al. | ............. 340/539.1 |
| 5,406,265 A | | 4/1995 | Trozzo et al. | ................ 340/632 |
| 5,446,445 A | | 8/1995 | Bloomfield et al. | ......... 340/521 |
| 5,481,181 A | | 1/1996 | McHardy et al. | ........... 324/71.1 |
| 5,553,094 A | | 9/1996 | Johnson et al. | .............. 340/637 |
| 5,568,121 A | | 10/1996 | Lamensdorf | ........... 340/539.17 |
| 5,597,534 A | | 1/1997 | Kaiser | ......................... 340/505 |
| 5,771,004 A | | 6/1998 | Suppelsa et al. | ............. 340/632 |
| 5,822,373 A | | 10/1998 | Addy | .......................... 375/259 |
| 5,861,316 A | | 1/1999 | Cage et al. | ..................... 436/52 |
| 5,969,623 A | * | 10/1999 | Fleury et al. | ................ 340/632 |
| 6,053,030 A | * | 4/2000 | Whynall et al. | .............. 73/23.2 |
| 6,114,964 A | | 9/2000 | Fasano | ......................... 340/632 |
| 6,169,488 B1 | * | 1/2001 | Ketler | ......................... 340/632 |

OTHER PUBLICATIONS

Gas Detection Systems Inc., publication entitled "Turn–Key Wireless Gas Detection", published prior to Oct. 14, 1998.
Gas Detection Systems, Inc. publication entitled "Stackpac", published prior to Oct. 14, 1998.
Gas Detection Systems, Inc. publication entitled "GDS–2000 Teledetection System", published prior to Oct. 14, 1998.
B & W Technologies Ltd. publication entitled "Wireless Multi–point Gas Monitoring–Rig Rat", published prior to Oct. 14, 1998.
Photographs (2) of Georgia Gulf Corporation installation in Louisiana prior to Oct. 14, 1998. Printing designating various components of the installation has been added to the photographs.

* cited by examiner

Primary Examiner—Van Trieu
(74) Attorney, Agent, or Firm—Tarolli, Sundheim, Covell & Tummino L.L.P.

(57) ABSTRACT

The current invention provides a wireless monitoring system. The system has one or more monitoring devices. Each device can transmit data and receive messages from an output center or alarm system. The output center can also transmit and receive messages. Both the output center and each device preferably have a transceiver that enables both the transmission and receipt of messages. No remote terminal units hardwiring is required for the system to function. The system is truly a wireless gas monitoring system. The system may use low earth orbit satellite technology, or licensed radio frequencies or any other means to wirelessly transmit and receive messages.

64 Claims, 17 Drawing Sheets

APPARATUS AND METHOD FOR WIRELESS GAS MONITORING

RELATED APPLICATIONS

This application claims the benefit of U.S. Provisional Applications No. 60/104,223 filed Oct. 14, 1998 and No. 60/122,863 filed Mar. 4, 1999. This application is a continuation-in-part of U.S. patent application Ser. No. 09/333,352 filed Jun. 15, 1999 and now U.S. Pat. No. 6,252,510.

FIELD OF THE INVENTION

This invention relates to the field of gas monitoring.

The invention provides a method and apparatus for wireless monitoring of gases, including toxic and combustible gases, with a device that has a radio transmitter that transmits quantitative gas levels to a master controller or multiple master controllers.

DESCRIPTION OF THE RELATED ART

Toxic gas monitoring systems are well known. Generally, gas monitors are placed around chemical producing facilities such as a chemical processing plant. These monitoring systems are configured to monitor for the presence of toxic and/or combustible gases. In addition to monitoring for the presence of these gases, typically in parts per million or lower explosive limits, these detectors could be configured to detect other important information such as wind speed and direction, temperature and other weather conditions. This information is then relayed to some sort of central reporting system. For instance, the information can be relayed back to the control center of a chemical plant and be displayed on a computer terminal or information sent directly to the plant's Distributive Control System.

Conventional toxic gas monitoring systems usually comprise multiple sensing units. These units are placed in and around the perimeter of a chemical processing plant, for example, to constantly monitor the targeted conditions around the plant. Upon detection of a toxic gas, usually at a predetermined level, the unit may sound an alarm in addition to relaying the information to the control center. This information can be used, for example, to determine the source of the gas so that an unexpected leak can be corrected. Alternatively, should the plant simply be operating at too high of a capacity and thus be generating too much toxic waste, its operations can be brought to within acceptable tolerances. Additionally, the wind speed, weather conditions and direction of the gas can be used to determine which people need to be warned about the presence of toxic gas and when such a warning should be issued.

Typically, in gas detection systems a master site provides information to a computer. U.S. Pat. Nos. 5,553,094, 5,568, 121 and 5,771,004 disclose such systems. U.S. Pat. No. 5,597,534 discloses a circuit that measures a chemical sensor output. Typically, specially designed software is incorporated as well. For example, the Gastronics' Event Scada Software is an unlimited tag Scada software which runs off Windows 95, 98 or 2000 or Windows NT and is designed for user friendliness along with the ability to customize and map out the geography of a plant. The Event Scada Software offers the user the flexibility to design and customize individual screens to match different applications. An assortment of tools allows the creation of trend charts, wind speed and direction, alarm settings and maintenance screens. A multilevel security feature may be included to prevent unauthorized access to customization functions.

Currently, the method of relaying this important information from the monitors to the control center has been through wires which physically connect each of the monitors to the output system. This is generally referred to as "hard wiring." Hard wiring requires each monitor to be physically connected to the output system by some sort of wire or cable. Hard wiring each of the numerous monitors to the control system can be quite costly, cumbersome and require substantial and frequent maintenance. For example, should the output system ever need to be relocated, such as in a different control room or outside of the plant, the cables would need to be rerouted to this new site. Rerouting all of the cables is labor intensive and expensive.

To further complicate matters, the wires may need to be buried in the ground (typically below the frost line) to comply with building code requirements or simply as a precautionary measure. Burying multiple wires in the ground requires substantial excavation which is rarely inexpensive. Similarly, repairing, replacing or moving these wires also requires substantial, expensive excavation.

Alternatively, the wires may need to be suspended at a height substantially above ground level. Such suspension may require the installation and maintenance of some sort of suspension devices, such as telephone poles. These poles would be placed in and around the chemical plant. This, again, may be an expensive undertaking. Finally, with regard to hard wiring, the wires themselves are usually expensive and are prone to breaking, cracking or failing in some sort of way. Thus, it is apparent that a wireless toxic gas monitoring system is desirable. The present invention comprises such a wireless toxic gas monitoring system.

It is common to monitor gas levels around large plants. Additionally, it is not uncommon for gas monitors to be placed some distance from these large plants. Consequently, the monitors may have to transmit information a substantial distance. Moreover, because the destination of this information is often located somewhere deep within the plant, e.g., a central control room, the monitors may need to relay this information through physical objects, such s layers of concrete, steel, insulation and other building materials.

In addition to physical barriers, the monitors usually need to transmit the information through substantial interference as well. Electric equipment and communication systems existing in almost all plants create vast amounts of interference such as electromagnetic waves, for example. Thus, a wireless gas monitoring system that is able to transmit information over a substantial distance and through substantial amounts of interference is desirable. The current invention utilizes, but is not necessarily limited to, licensed radio frequencies that operate at higher powers and are therefore able to transmit over large distances and through substantial amounts of interference.

Radio telemetry has recently been used as a lower cost alternative to hard wiring the monitors to the output or control systems. A typical radio telemetry system using RTU's, while reducing significant installation costs, still requires both the high cost of the RTU as well as the installation costs to wire the gas monitors to the RTU. With the advent of the current invention, the advantages of wireless toxic gas monitoring systems are realized. This particularly true with respect to very long conduit runs, such as with perimeter monitoring applications, where the cost of the RTU and wiring the sensors to the RTU is increased by the long lengths of the conduit and installation costs.

Additionally, most monitors of the related art are event triggered only. By this it is meant that the monitors only relay a signal when they detect a high level of gas. The monitors merely let you know when a threshold level of gas (such as a gas denoted "alpha") has been surpassed. For instance, if a system were set to detect 0.5 ppm of gas alpha but a dangerously high level of 20 ppm of gas alpha existed around the plant, the detector would only transmit a signal telling the controller that an amount of gas alpha above 0.5 ppm had been detected. However, the actual concentration, i.e. the dangerously high 20 ppm of gas alpha, would not be relayed back to the control room. This type of system would not provide and quantitative documentation which may be useful in any number of situations.

Thus, a wireless gas monitoring system with heightened sensitivity is desirable. By this it is meant that it would be desirable to have monitors that monitor and relay more detailed information. The current invention does just that. The monitors will not only relay the actual amount of gas detected, i.e. 20 ppm, but they may also relay operating parameters of the system such as the battery voltage, day, date, time, wind speed, weather conditions, etc. existing at the time the gas was detected.

From the foregoing it is clear that certain improvements are desired. Many of the desired improvements have been accomplished by the current invention.

The present invention contemplates a new and improved method and apparatus for wireless gas monitoring which is simple in design, effective in use, and overcomes the foregoing difficulties and others while providing better and more advantageous overall results.

SUMMARY OF THE INVENTION

The current invention is a system for wireless toxic gas monitoring with a monitoring device that eliminates the RTU by integrating the radio transmitter directly into the gas monitor, thus making it integral with the device. Although the current invention may utilize licensed UHF radio transmissions, the device is not limited to the type of radio, whether it be land based, cellular or satellite, the strength or radio or any safety approval classifications.

The transmitters feature a unique method of wireless monitoring that eliminates not only the high installation costs of hardwired systems, but also the cost of wireless Remote Terminal Units (RTU's). A typical perimeter gas monitoring system, where the monitors are completely hardwired to the master site, costing in the neighborhood of $400,000 may only cost $200,000 if the monitors are hardwired to RTUs and the RTUs transmit via radio to the master. The current invention which has the transmitters integral with the monitors would reduce the cost of this system to approximately $100,000 by eliminating the RTU's and the associated costs of installation and installation materials.

One advantage of the current invention is that the licensed radio frequencies enable the current invention to operate at higher powers. This allows the monitors of the current invention to transmit information over large distances and through substantial amounts of interference.

Another advantage of the current invention is the fact that it is wireless. This permits toxic gas monitoring and installation to be performed in an inexpensive manner not requiring substantial and frequent maintenance.

Yet another advantage of the current invention is the fact that remote transmitters are integrated into the monitors of the current invention. This enables equipment, maintenance, labor, manufacturing and installation costs and expenses to be reduced.

Still another advantage of the current invention is the fact that each of the monitoring devices and the output center may comprise a transceiver. The transceiver can both transmit and receive messages. Separate transmitters and receivers are therefore not needed and costs are thereby reduced.

Another advantage of the current invention is its heightened sensitivity. Upon detection of a gas, the monitors monitor and transmit a substantial amount of detailed information.

Still other benefits and advantages of the invention will become apparent to those skilled in the art upon a reading and understanding of the following detailed specification.

A plurality of gas monitor stations are provided at locations which are spaced from a potential source of a selected gas whose presence is to be detected. Each of the gas monitor stations includes a gas sensor assembly, a control assembly, a radio, and data entry apparatus. The data entry apparatus may be a keypad which is manually actuated. However, the data entry apparatus may include magnetically actuated switches and/or a remote control unit. A display is provided at each gas monitor station to provide for visual review of data entered at the gas monitor station.

In response to a predetermined condition, radio transmission to a master station is initiated from any one of the gas monitor stations. The predetermined condition which results in initiation of radio transmission may be one or more of a plurality of different conditions. The conditions which result in initiation of radio transmission may be varied by actuating the data entry apparatus to change data stored in the control assembly at each of the gas monitor stations.

The conditions which result in initiation of radio transmission from any one of the gas monitor stations may include one or more of the following conditions:

(a) Sensing of a predetermined concentration of the selected gas in the atmosphere at the gas monitor station.

(b) Sensing of a predetermined change in the concentration of the selected gas in the atmosphere at the gas monitor station. The change in the concentration of the selected gas may be either an increase or a decrease in the concentration of the selected gas.

(c) The elapse of a predetermined maximum length of time since the last radio transmission was made.

(d) Determining that a moving average of sensed concentration of the selected gas exceeds a predetermined magnitude.

(e) Determining that a battery, which supplies current for the radio, has an output voltage which is less than a predetermined voltage.

(f) A change in battery voltage by a predetermined amount.

It should be understood that the data entry apparatus at each of the gas monitor stations may be utilized to select any one or more of the foregoing conditions or other conditions not set forth above, to initiate radio transmission from a gas monitor station while omitting other conditions. The data entry apparatus may also be utilized to enter data corresponding to parameters, that is, limits, utilized in association with each of the conditions which initiate radio transmission from a gas monitor station to a master station. The sensor assembly at each of the gas monitor stations may be calibrated by exposing the sensor assembly to a known concentration of the selected gas. This may be done by exposing the sensor assembly to a container of gas or gas-generating device, such as a permeation tube calibrator or gas generator.

The data entry apparatus is actuated to adjust data set forth on a display at the gas monitor station to correspond to the known concentration of the selected gas.

Once the sensor assembly has been calibrated, the sensor assembly may be checked by applying a predetermined voltage to the sensor assembly.

In order to eliminate the effect of transient conditions, such as puffs of the selected gas, the sensor reading at a gas monitor station is averaged over a predetermined period of time. This period of time may be relatively short, for example, thirty seconds or less. The predetermined period of time over which the sensor readings are averaged may be entered into the control assembly by actuating the data entry apparatus at a gas monitor station.

It should be understood that anyone of the features of the invention may be used separately or in combination with other features. It should be understood that features which have not been mentioned herein may be used in combination with one or more of the features mentioned herein.

BRIEF DESCRIPTION OF THE DRAWINGS

The invention may take physical form in certain parts and arrangement of parts. A preferred embodiment of these parts will be described in detail in the specification and illustrated in the accompanying drawings, which forms a part of this disclosure and wherein.

DESCRIPTION OF ONE SPECIFIC PREFERRED EMBODIMENT OF THE INVENTION

Figure 1:
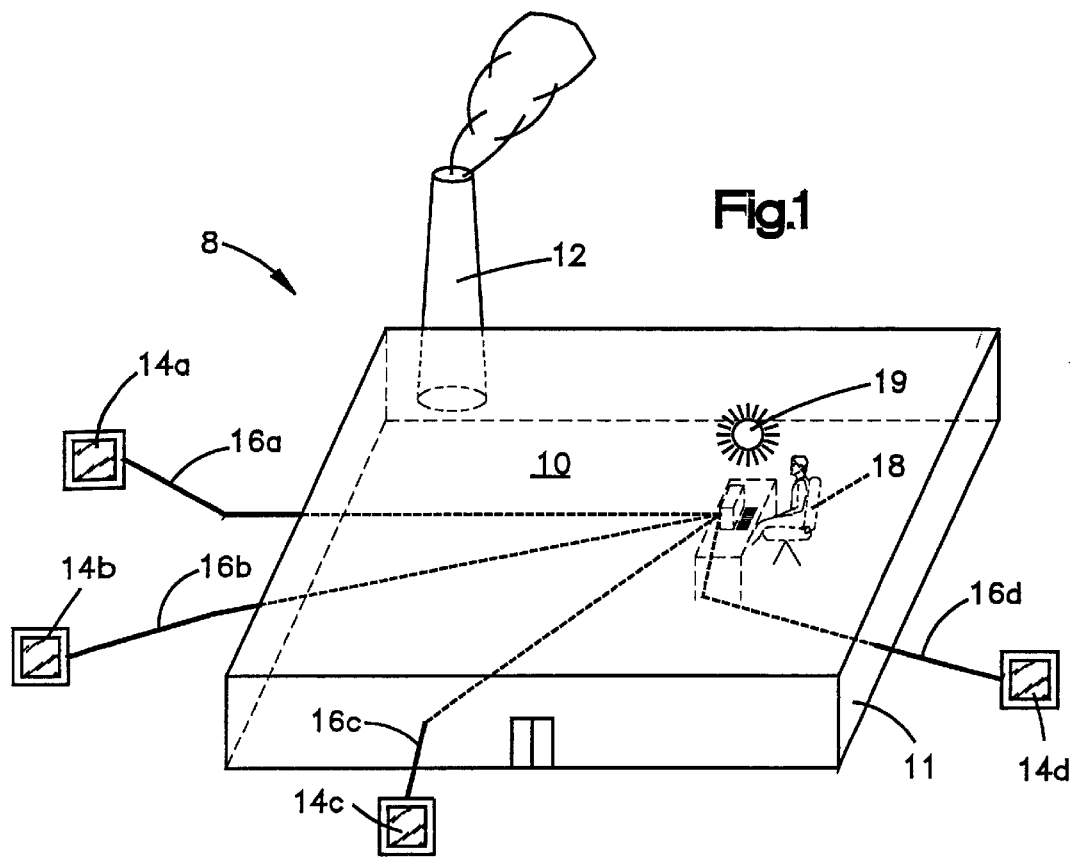
FIG. 1 shows a gas monitoring system of the related art wherein the gas monitors are hard wired to the control center of a plant.
Figure 2:
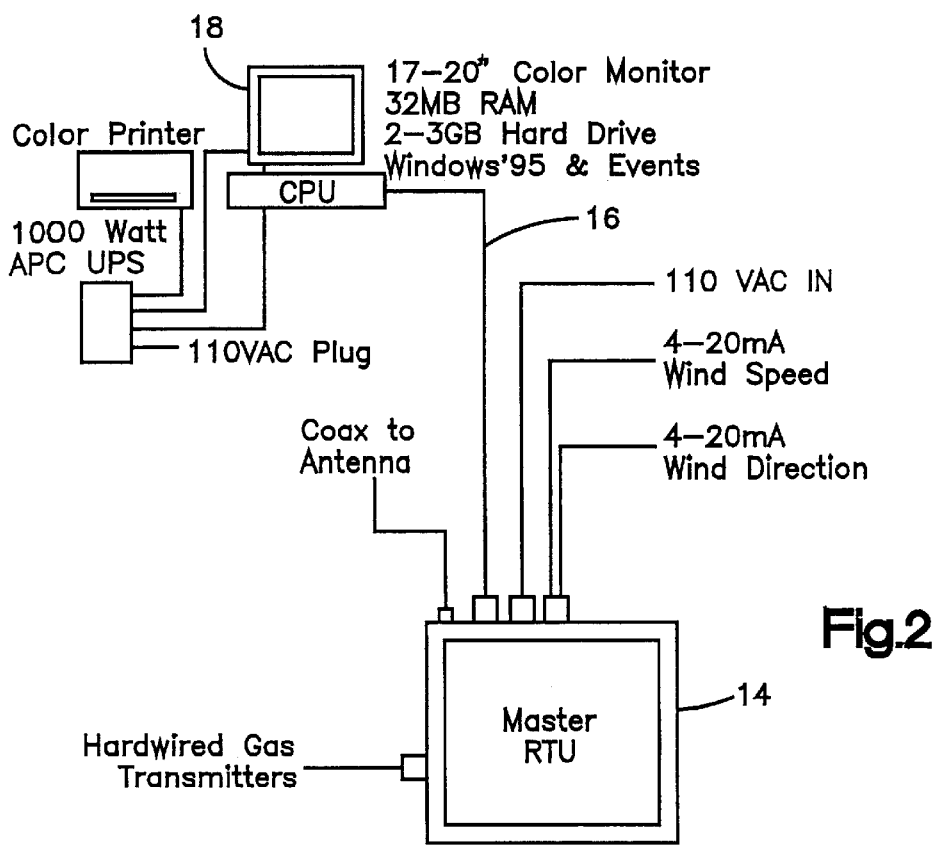
FIG. 2 is an alternative depiction of a gas monitoring system of the related art wherein the gas monitors are hard wired to the control center of a plant.

Referring now to the drawings, which are for purposes of illustrating a preferred embodiment of the invention only, and not for purposes of limiting the invention, FIG. 1 shows a chemical processing plant 10. The plant 10 is depicted as having a discharge means 12. The discharge means 12 are a potential source of a selected gas. Multiple toxic gas monitors or monitor stations 14a, 14b, 14c 14d are placed around the plant 10. FIGS. 1 and 2 show the previous technology wherein each monitor or station 14a, 14b, 14c, 14d had to be hard wired via cables 16a, 16b, 16c, 16d to the control center or master station 18. Should control center or master station 18 need to be relocated at a different site, such as outside of the plant 10, the cables 16a, 16b, 16c, 16d would need to be extended to this remote site. Such a configuration and any changes to such a configuration were expensive, labor intensive and required substantial frequent maintenance.

Figure 3:
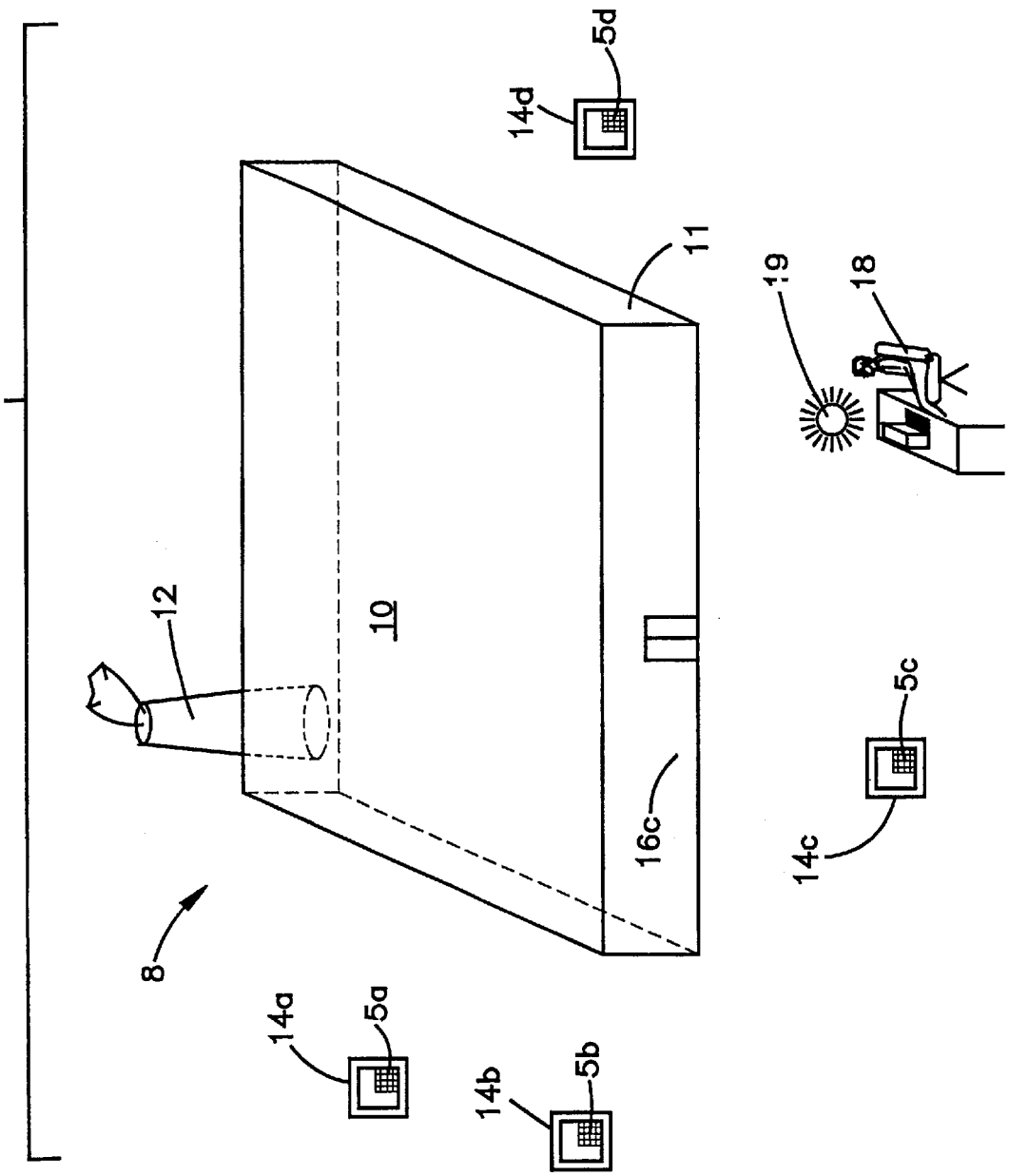
FIG. 3 shows the wireless gas monitoring system of the current invention wherein the transmitters are integral with the monitors.

FIG. 2 depicts the interconnection of some of the equipment of related art gas monitoring systems. FIG. 2 also gives some specifications on some of this equipment. Note that, in operation, the gas monitoring system 8 (FIG. 3) of the current invention may utilize much of the same equipment. However, most of the interconnection of this equipment will be by way of radio frequencies rather than wire cables 16a, 16b, 16c, 16d (FIGS. 1, 2 and 3). The inventive system disclosed herein has advantages over the related art because, in addition to having all of the hardware, software and other elements necessary to monitor around the plant, the transmitters are integral with the monitors 14. Thus, no hardwiring and RTU's are necessary.

Figure 4:
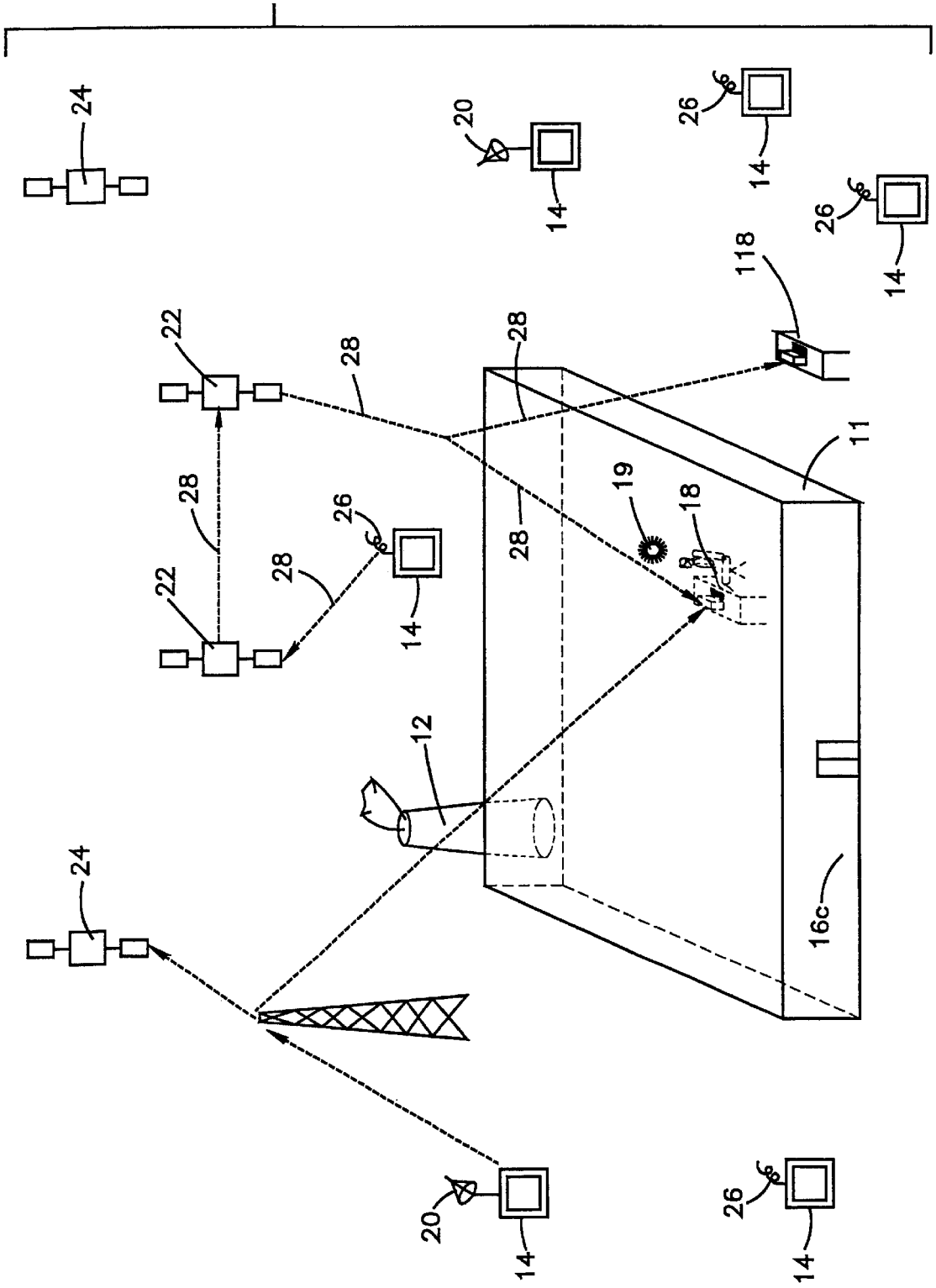
FIG. 4 shows the current invention utilizing cellular and/or low earth orbit (LEO) satellite technology.

FIG. 4 shows a chemical plant 10 with monitors 14 around the plant. Monitors 14 employing radio telemetry are depicted comprising satellite dishes 20. In the past, in order to have wireless connection to the control center 18, each monitor or station 14 needed to employ an antenna more powerful than a cellular phone antenna Additionally, these antennas needed to have a higher gain than that of a cellular phone antenna. These requirements were usually met by a remote terminal unit that sometimes included a satellite dish. Prior to the advent of low earth orbit (LEO) satellite technology, these large dishes were necessary because previous satellites were at a higher altitude and had orbits different from low earth orbit satellites 22. Because the prior satellites were at higher altitudes and had different orbits, an antenna with a higher gain, such as a satellite dish, was required for communication between the satellite 24 and the monitor or station 14 on the ground. These remote terminal units were bulky and expensive. Should the current invention utilize low earth orbit satellite technology, the gas monitors or stations 14 need only comprise a small antenna 26 similar to a small cellular phone antenna to communicate with the low earth orbit satellites. Thus, the current invention permits an inexpensive, reliable and virtually maintenance free wireless connection to be made to the control center or master station 18. Compared to the related art, the current invention I provides a substantially smaller and less expensive detection system.

When utilized in conjunction with LEO technology, the small wireless antenna 26 employed in the toxic gas monitoring devices or gas monitor stations 14 of the current invention transmit a wireless data message comprising information such as gas detected, wind speed and wind direction. The data message is transmitted to a LEO satellite 22 where it may be linked to a local gateway for validation and optimal routing to the recipient which would be the control center or master station 18. This transmission pathway is depicted as lines 28 in FIG. 4. With this wireless technology, the control center 18 may be easily and conveniently located and relocated without the inherent difficulties of hard wiring or moving cumbersome and expensive equipment. For demonstrative purposes, FIG. 4 depicts control center 118 being located outside of plant 10.

When operating with LEO technology, a monitor 14 transmits information regarding a change in toxic gas detected by way of the low earth orbiting satellites 22 to the control center 18. This information is transmitted repeatedly as changes in reading occur. However, once the monitor 14 no longer detects toxic gas at a predetermined level, the transmitter preferably stops transmitting and waits for the next changed reading.

Additionally, the control center 18 may have the ability to transmit as well as receive data messages. For instance, the control center 18 may periodically poll each monitor 14 for supervisory purposes. Thus, each monitoring device 14 may also have the ability to receive as well as transmit wireless data messages, such as in the form of polling messages, for example.

With low earth orbit satellites, more than one monitor 14 of the wireless toxic gas monitoring system of the current invention can interactively relay data messages. Each and every one of the monitors 14 can simultaneously transmit data messages to the low earth orbit satellites and the satellites will carry through and deliver the entire data message too the control center 18. Because of this capability, low earth orbit technology offers the advantage of not missing transmissions and information.

FIG. 3 shows the preferred embodiment of the current invention that does not use satellite technology. A chemical plant 10 is shown with gas monitor stations 14a, 14b, 14c, 14d of the current invention around the plant. In this embodiment, the transmitters are integral with the monitor stations 14. A wireless data message comprising information such as the actual amount of gas detected, battery voltage, wind speed, wind direction, etc. 36 is transmitted from the gas monitor stations 14a, 14b, 14c, 14d to the control center 18. It is contemplated that the gas monitor stations 14a, 14b, 14c, 14d may be constructed without including apparatus to monitor wind speed and/or wind direction. With this wireless technology, the control center 18 may be easily and conveniently located and relocated without the hassle of hard wiring or moving cumbersome and expensive equipment. For demonstrative purposes FIG. 3 depicts control center or master station 18 being located outside of plant 10. A mobile control center of master station 18 may be provided if desired.

Figure 5:
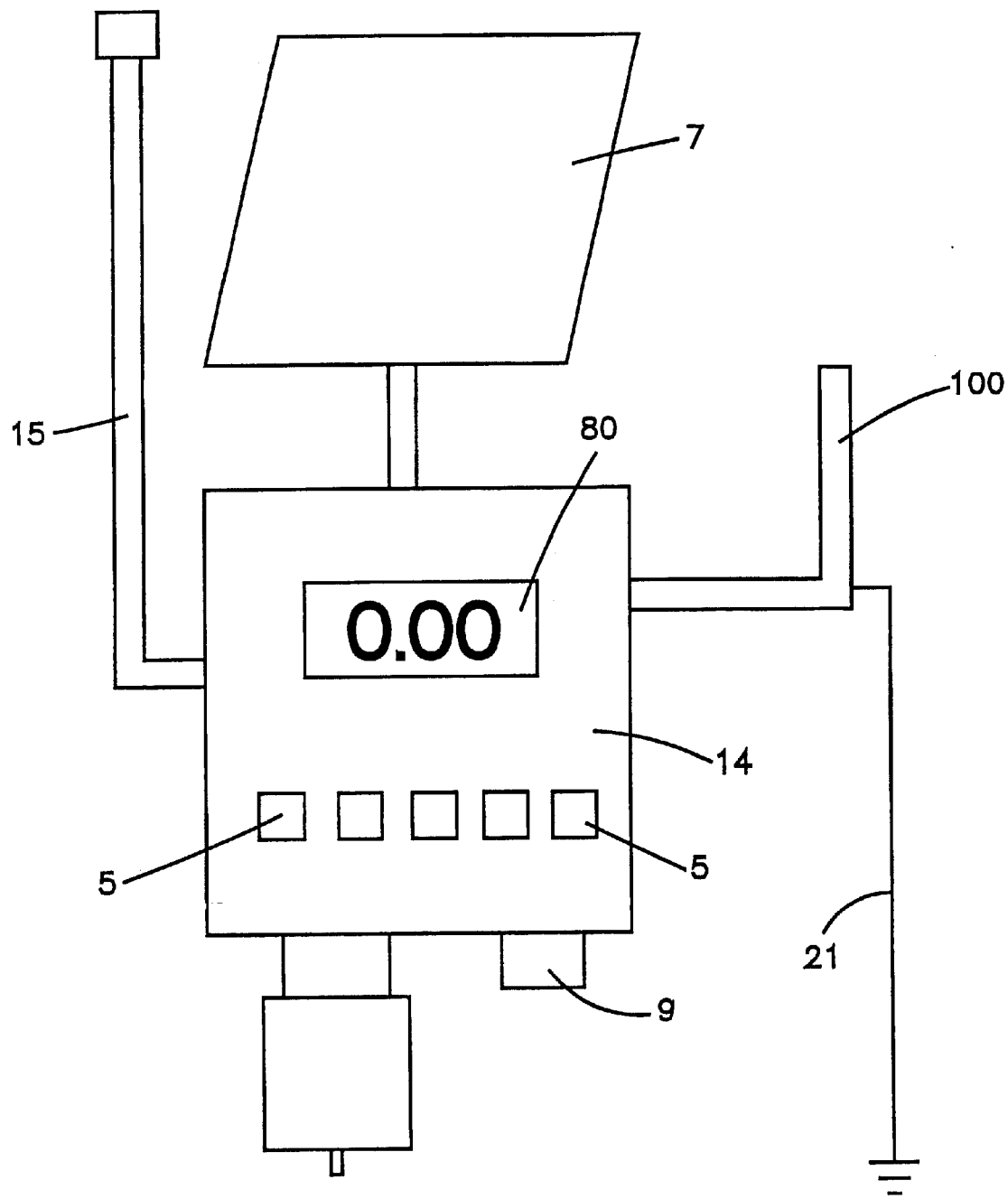
FIGS. 5 and 5a shows the preferred embodiment of the current invention utilizing radio and solar technology.
Figure 5A:
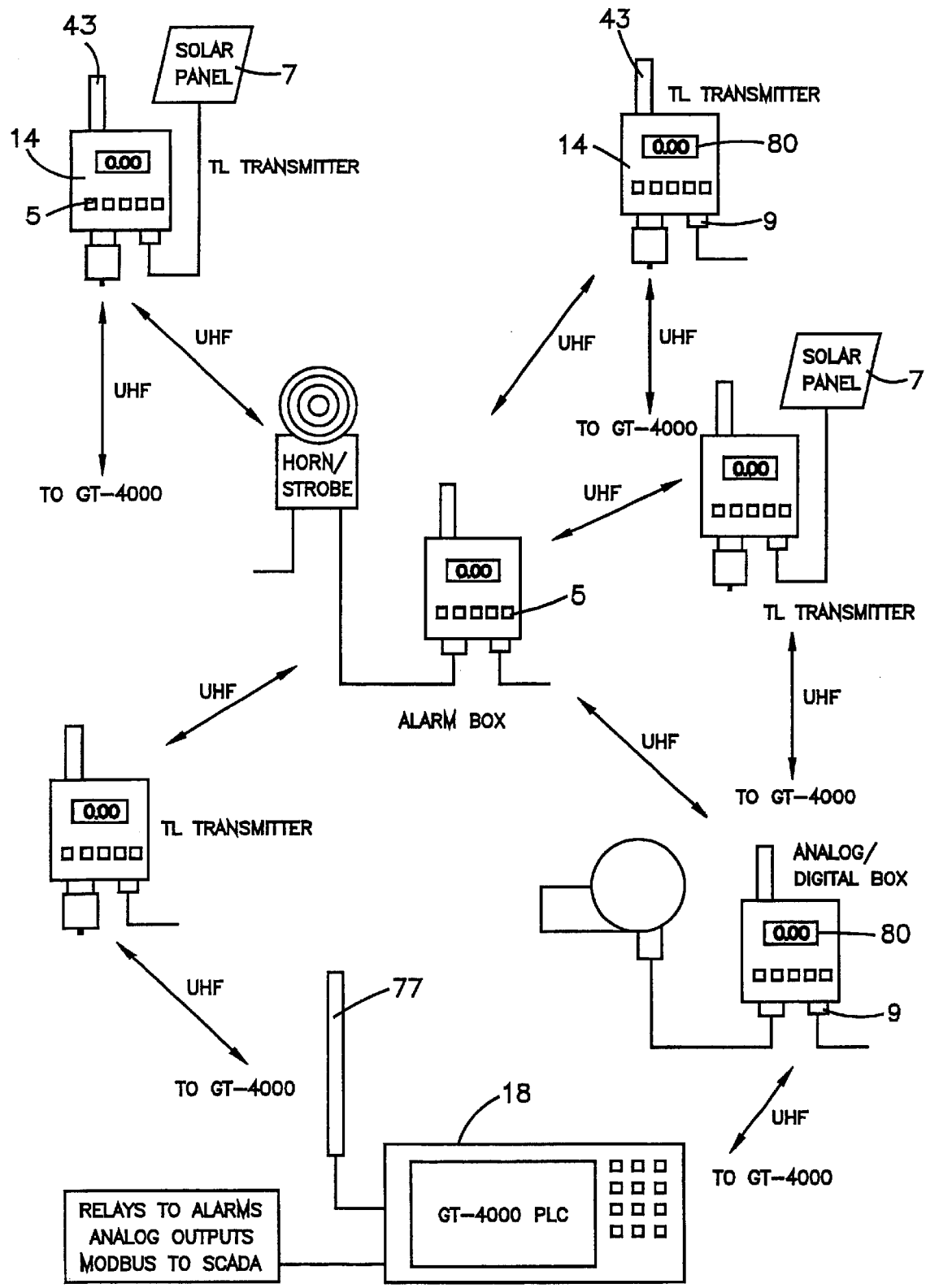

So that the system may be further wireless, applicant envisions that the monitors or gas monitor stations 14a, 14b, 14c, 14d may be solar 7 or battery 9 powered (FIGS. 5 and 5a) or powered by any other source of power chosen with sound engineering judgment. In the preferred embodiment, each monitor comprises a 4 amp lead acid battery capable of supporting the system a nominal operation for up to five days without power as well as a 20 watt solar panel. Additional battery power is optional. Preferably, the monitoring devices operate properly at temperature range between −40 degrees C. to +50 degrees C. It is also preferred that the monitors are shielded against lightning strikes through a lightning arrestor 100 combined with a copper ground rod 21 (FIG. 5). It is further preferred that the solar panel be 5 inches by 13 inches and that each monitoring device be comprised with a 6 inch by 6 inch housing.

With continuing reference to FIG. 3, the gas monitoring system 8 disclosed herein may operate at any frequency, but preferably utilizes licensed radio frequencies. Licensed radio frequencies provide better and more advantageous overall results than the radio frequencies used in the related art. This is because nonlicensed radio frequencies operate at lower power than licensed radio frequencies. The lower powered nonlicensed radio frequencies are unable to transmit data from the monitors 14a, 14b, 14c, 14d to the control room 18 typically located inside the plant 10. Additionally, the nonlicensed radio frequencies are unable to transmit over substantial distances or through substantial interference. The monitors 14a, 14b, 14c, 14d disclosed herein can transmit detailed information over substantial distances and through substantial amounts of interference.

The monitors 14a, 14b, 14c, 14d disclosed herein can accurately transmit information through walls 11 as well as interference in the form of electromagnetic waves, for example. These particular types of interferences and impedances are encountered in almost all gas monitoring applications. This is because the destination of the information transmitted by the monitors 14a, 14b, 14c, 14d is usually located somewhere within the plant 10. Typically, the control room 18 is centrally located somewhere deep within the plant 10. Consequently, the monitors 14a, 14b, 14c, 14d must transmit the data through physical barriers of the plant 10 such as concrete and steel walls 11. Additionally, this information must successfully traverse interference created by electric equipment and communication systems. Such interference typically presents itself in the form of electromagnetic waves which exist within virtually all plants 10.

The licensed radio frequencies disclosed herein may be obtained by way of application to the federal Communications Committee "FCC". Applicant notes that a particularly useful bandwidth of licensed radio frequencies would be between 450–470 megahertz "mHz". Preferably, the current invention operates within this bandwidth. Preferably, the transmitters 42 that are integral with the monitoring devices 14 comprise an up to a 5 Watt 450–470 mHz (UHF) radio transmitter. This eliminates the need for wiring to a Remote Radio Terminal Unit (RTU), thereby significantly reducing costs.

Regardless of the frequency used, the current invention, even without the use of satellite technology, will not miss transmissions. This is because each monitoring device 14 will very rapidly transmit its readings to an output center. Because these transmissions occur so often, there is insufficient time for data readings to accumulate between transmissions.

The gas monitor stations 14 may comprise more than one sensor 38 to sense various gasses. In the preferred embodiment, the gas sensor 38 may be an electrochemical, infrared or catalytic gas sensor. Some of the sensors may operate in the range of 4 mA to 20 mA. Preferably, the gas detection system 8 disclosed herein comprises means 5 (FIG. 5) to interface with each monitor 14a, 14b, 14c, 14d (FIG. 3). Preferably, this is an easily accessible keypad 5a, 5b, 5c, 5d on the face of each monitor 14a, 14b, 14c, 14d. This keypad 5a, 5b, 5c, 5d allows the monitoring devices to be manipulated. For instance, they may enable the monitoring devices 14a, 14b, 14c, 14d to be programmed for the particular type of gas to be monitored for as well as the level of this gas which causes the monitors to start transmitting information.

Figure 6:
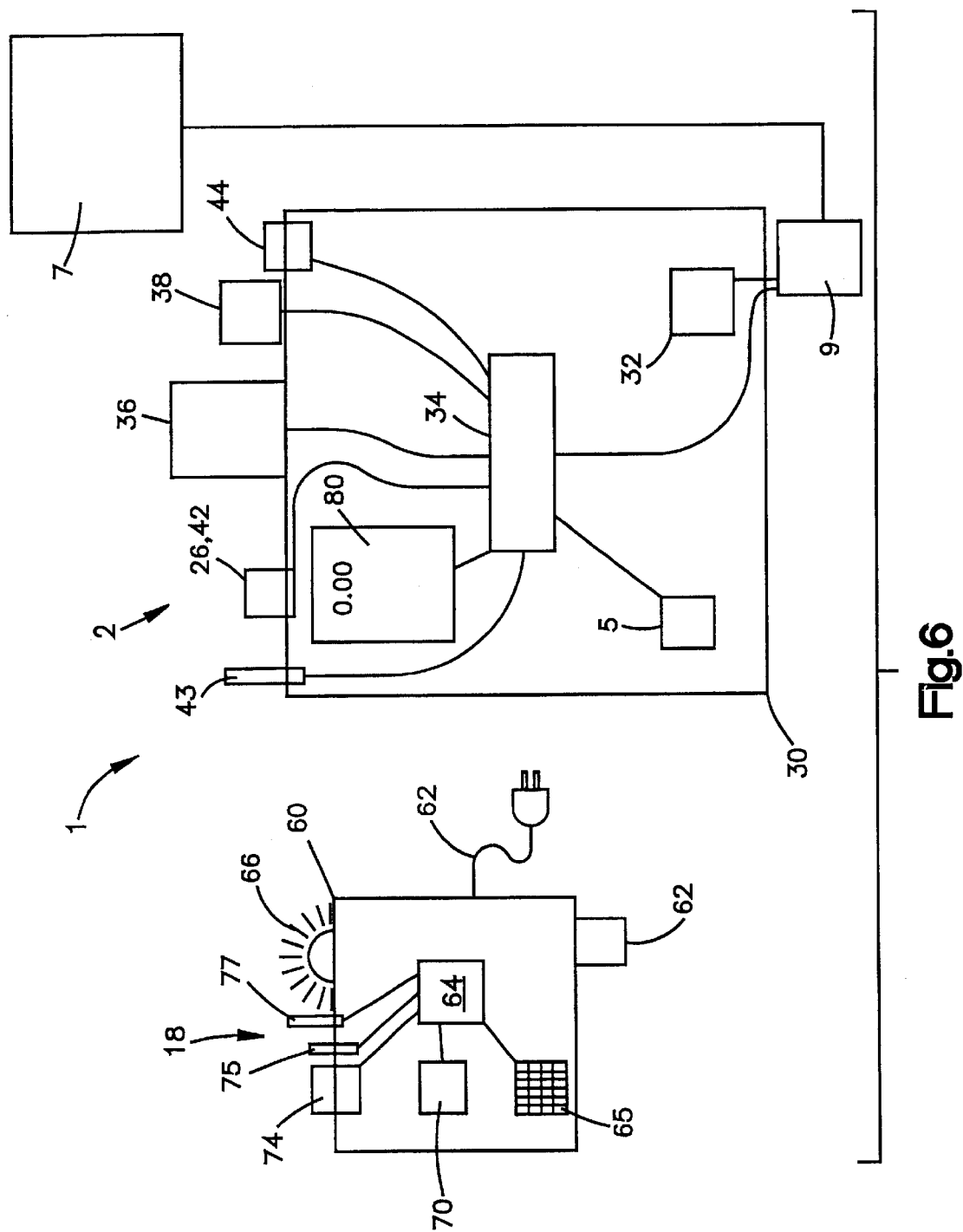
FIG. 6 shows another preferred embodiment of a monitoring device of the current invention.

Preferably, each monitoring device 14 comprises a display 80 (FIG. 5). Each device can be configured so that any number of readings taken by the device are displayed on the display 80. With reference to FIG. 6, each monitoring device also comprises a microprocessor 34 for driving the display 80 and causing the appropriate reading to be displayed on the display 80. The microprocessor 34 also enables a user to interface with the device via the interface means 5. Preferably, the microprocessor links the display 80 and the interface means 5 so that the display 80 is useful in assisting a user to interface with the monitoring device 14. It is further preferred, that the microprocessor 34 monitors sensor readings and initiates and controls transmissions. Optionally, the microprocessor may cause the monitoring device to periodically transmit polled data readings.

Additionally, it is preferred that the monitoring devices 14a, 14b, 14c, 14d are reprogrammable. By this it is meant that the monitors 14a, 14b, 14c, 14d may be used time and again for the detection of different gases. It is further preferred that via the interface means 5 selective monitoring may be accomplished. By this it is meant that the particular condition(s) to be monitored for may be selected and the monitoring devices 14a, 14b, 14c, 14d calibrated and configured accordingly. It is preferred that the monitoring devices can at least monitor for chlorine, ammonia, hydrogen fluoride, hydrogen cyanide, phosphine, fluorine, chlorine dioxide, phosgene, carbon monoxide, ozone, diborane, methyl mercaptan, hydrogen sulfide, sulfur dioxide, hydrazine, silane and germane at a plurality of concentrations. An alternative embodiment within the scope of the invention has a receiver 44 connected to the microprocessor 34. The receiver 44 allows remote transmissions to be received by the monitoring device 14. This may allow, for example, the operating parameters of the monitoring device to be reprogrammed from a remote location.

For optimum performance, simplicity and efficiency, it is preferred that the transmitter 42 and receiver 44 are integrated into a single component known as a transceiver 43 (FIG. 6). In this fashion, each monitoring device 14 is very compact and is literally a remote transmitting unit as well as a remote receiving unit. The monitoring devices 14 then do not require remote terminal units RTU's to transmit or receive data messages. The cost of toxic gas monitoring is thereby significantly reduced.

In operation, preferably the monitors "sleep" unless a change causes them to transmit. By this it is meant that the monitors do not transmit data unless a preprogrammed level of a particular gas is detected or upon a battery voltage change or in reply to a transmission from the master site(s). Once this event occurs, the monitors begin to transmit data. The monitors 14a, 14b, 14c, 14d transmit information regarding changes in gas detected. This information is transmitted repeatedly as changes in readings continue. However, once the monitors 14a, 14b, 14c, 14d no longer detect gas at a predetermined level, the monitors 14a, 14b, 14c, 14d again rest and wait for the next changed reading. Upon a subsequent changed reading that exceeds the predetermined threshold level, the monitors once again begin to transmit information. According to another embodiment of the invention, the control center 18 may periodically poll each monitor 14a, 14b, 14c, 14d for supervisory purposes.

The monitors of the current invention allow the transmission of information which may be quantified. By this it is meant that the monitors transmit detailed information. The monitors transmit not only the actual amount of gas detected but also the status of important surrounding circumstances. For instance, this information may include the parts per million (ppm) of gas detected, explosion limit levels, battery voltage (voltmeter 32), alarm statuses, date, time, wind speed, wind direction (weather sensing means 36), etc. existing at the time the gas was detected.

According to another embodiment of the invention, upon detection of a toxic gas, usually at a predetermined level, the system may sound an alarm box 19 (FIG. 3). The alarm may be sounded alone or in addition to relaying the aforementioned information to the output center 18. Alternatively, the master site may only be the alarm boxes rather than an output center 18. Additionally, alarms 19 could also be on the monitors 14 and/or in the control room 18. Preferably, the alarm box is a 5 Watt UHF radio receiver device providing 3 amp to 10 amp rated relays that are synchronized to the alarm settings of the transmitters.

Preferably, the output center or master station 18 has a receiver 74 for receiving transmissions from a monitoring device or gas monitor station 14. The output center 18 also has a housing 60, microprocessor 64, and power means 62 for powering the output center. Additionally, the output center 18 has a display 70 and interface means 65. Preferably, the microprocessor 64 connects the receiver 74, display 70, interface means 65 and signaling means 66 for producing a signal. The signal may be an audible or visual signal that signal the detection of a certain gas.

As mentioned above, the output center or master station 18 may periodically poll each monitoring device or gas monitor station 14, such as for supervisory purposes, for example. Thus, as with each monitoring device 14, the output center 18 preferably can transmit as well as receive data messages. To effect this the output center 18 may have a transmitter 75 operatively connected to the microprocessor 64. However, for optimum compactness and operating efficiency, again as with each monitoring 14, the output center 18 has a single transceiver 77 that both transmits and receives data messages (FIG. 6). This eliminates the need for the output center 18 to have both a transmitter 75 and a receiver 74.

Preferably, each monitoring device 14 has its own housing 30 and site address with respect to the rest of the system. This address distinguishes one monitoring device from another. Preferably, each monitor can be tied into other detection systems by providing an ASCII formatted RS232 signal to a DCS. Since many DCS systems require Modbus for their driver, the Master RTU is often directly compatible. Analog outputs for each transmitter can be provided through the use of an analog output expansion card.

Reliable and appropriate sensor technology will be incorporated into the system. A couple of sensor manufacturers, with whose products the current invention performs optimally, are Sensoric and GmbH. Some benefits of the sensors used in the current invention are: no temperature effects, no humidity effects, no periodic zeroing required, no background current, greater chemical selectivity, no drying out, no taking on moisture, no costly recharges or refilling of electrolyte.

Specifications regarding the one specific embodiment of the current invention are as follows:

| | |
|---|---|
| Housing | Nema-4X (Optional Explosion Proof Version |
| Temperature Range | −40° C. to +50° C. |
| Humidity Range | 0–100% RH |
| Power Options | 115/220 VAC or 12 VDC Solar Powered |
| Power Consumption | 40 mA Nominal, 1000 mA during transmission |
| Internal Battery | 12 VDC, 4 Amps |
| Radio Power | 2 watts or 5 watts |
| Antenna Gain | 3 db |
| Radio Frequency | UHF Licensed, Provided by Gastronics |
| Frequency Adjust | Crystals |
| Microprocessor | 32 bit |
| Analog Resolution | 16 bit |
| Keypad Settings | Trigger on Change, Drop Out, Analog Filtering, STEL/Hi/HIHi Alarms, Remote Site Address, Master Site(s) Address, Alarm Box Site Address |
| Jumper Settings | Display Resolution, Sensor Type, Sensor Range |

Figure 7:
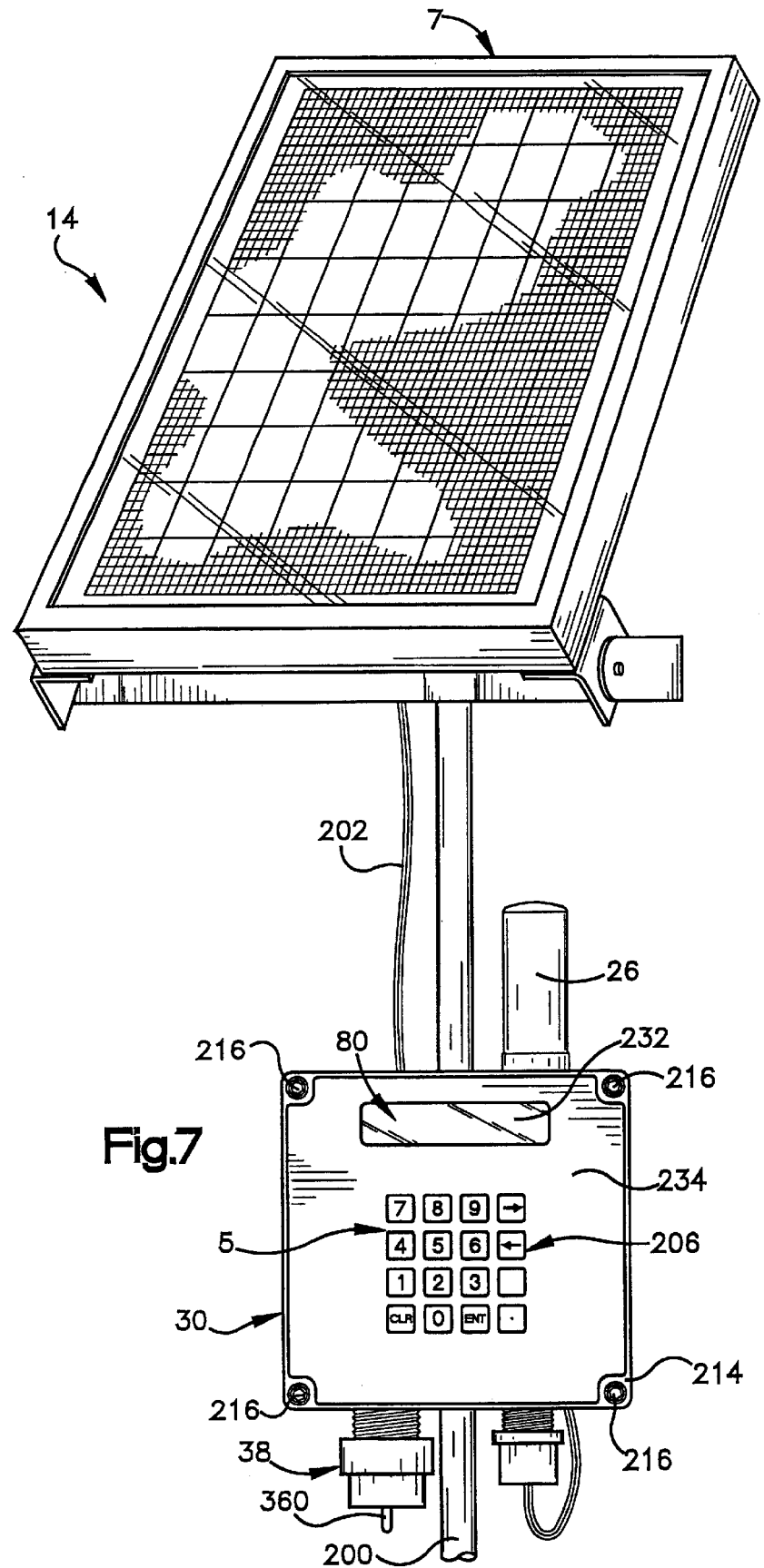
FIG. 7 is a pictorial illustration of one gas monitor station of a plurality of gas monitor stations which are disposed at selected locations spaced from a potential source of a selected gas.

A gas monitor station 14 is illustrated in FIG. 7 of the application drawings. The gas monitor station 14 is one of a plurality of identical gas monitor stations which are disposed at selected locations spaced from a potential source 12 of a selected gas. The gas monitor stations 14 may be arrayed around a potential source 12 of a selected gas in the manner illustrated in FIG. 3. Alternatively, one or more of the gas monitor stations 14 may be located inside the plant 10. The master station 18 may be located outside the plant 10, as shown in FIG. 3, or located inside the plant, as shown in FIG. 4.

The environment around the source 12 of the selected gas is monitored for the presence of the selected gas by the gas monitor stations 14 (FIGS. 3 and 4). The gas monitor stations 14 (FIGS. 3 and 4) may all have the same construction and mode of operation as the gas monitor station 14 of FIG. 7. However, the gas monitor station 14 of FIG. 7 is not equipped to cooperate with satellites 22 and 24 (FIG. 4). If desired, the gas monitor station 14 of FIG. 7 could be equipped to cooperate with satellites.

Upon the occurrence of a predetermined condition, for example, the sensing of a predetermined concentration of the selected gas in the atmosphere adjacent to a gas monitor station 14 (FIG. 7), a radio in the gas monitor station transmits to a master station or control center 18 (FIG. 3). Although it is believed that it may be desired to have the master station or control center 18 in a building or plant 10 and the gas monitor stations 14 disposed in an array about the building, one or more of the gas monitor stations could be provided within the building.

The master station or control center 18 may be a stationary control center disposed within the building or plant 10 which provides the source of the gas which is to be detected by the gas monitor stations 14. However, the master or control station 18 could be disposed at a location which is remote from the source of the gas which is to be detected. The potential source of gas could be outside of any building. Although only a single master station or control center 18 has been illustrated schematically in FIG. 3, it should be understood that a plurality of master or control stations could be provided if desired.

It is contemplated that a stationary master station 18 could be provided within the building 10 and a mobile or secondary master station (not shown) could be provided in a vehicle which is capable of traveling to the gas monitor stations 14. Data from the gas monitor stations 14 could be utilized to plot, on a suitable display, the probable configuration of a cloud of gas from the potential source 12 of gas. This would enable the mobile master station to approach one of the gas monitor stations 14 from a direction which would minimize exposure of occupants of the vehicle containing the movable master station or control center to a gas from the potential source 12 of gas. It is contemplated that radio communications would be maintained between the mobile master station 18 and the stationary master station which may be disposed within the building 10.

It should be understood that the gas monitor stations 14 could all be provided within the building 10 if desired. A stationary master station 18 could be provided in the building 10 along with the gas monitor stations 14. Alternatively, the master station 18 could be disposed at a location remote from the building 10 and the potential source 12 of gas. A mobile master station could be provided within the building 18 in a movable housing which may be carried by an individual, such as a technician, to any one of the gas monitor stations in the building.

The gas monitor station 14 illustrated in FIG. 7 is intended to be located in the environment around and spaced from the source of the gas to be monitored. Thus, the gas monitor station 14 would be mounted at a location remote from the building 10 and the master station 18 in the manner illustrated schematically in FIG. 3. The gas monitor station 14 is constructed in such a manner that being outdoors in the environment around a source of gas will not result in degradation of the operating characteristics of the gas monitor station. However, the gas monitor station 14 could be disposed in the building 10 if desired.

The gas monitor station 14 includes a housing 30 (FIG. 7) which is connected with a stationary mounting post or rod 200. A solar panel 7 is mounted on the post 200 above the housing 30. The solar panel 7 is positioned to face toward the sun. The sun's rays activate the solar panel 7 to provide energy for the gas monitor station 14. The solar panel 7 is connected with the housing 30 by a cable 202.

The gas monitor station 14 includes a gas sensor 38 (FIG. 7) which is fixedly connected to the housing 30 and is exposed to the atmosphere around the housing. In the embodiment of the gas monitor station 14 illustrated in FIG. 7, the gas sensor 38 is disposed outside of and is connected to the housing 30. If desired, the gas sensor 38 could be enclosed in the housing and exposed to the atmosphere adjacent to the housing by suitable openings within the housing. If desired, a pump could be provided to induce air adjacent to the housing 30 to flow into the housing. Alternatively, the gas sensor 38 could be spaced from the housing 30 and connected with the housing by a suitable cable, in much the same manner as in which the solar panel 7 is connected with the housing 30 by the cable 202.

Data entry apparatus 5 (FIGS. 7 and 14) is connected with the housing 30 (FIG. 7) and is exposed to the environment around the housing. Therefore, the data entry apparatus 5 is constructed in such a manner that exposure of the data entry apparatus to the environment around the gas monitor station 14 does not result in malfunctioning of the data entry apparatus. In the embodiment of the invention illustrated in FIG. 7, the data entry apparatus 5 includes a keypad 206 which is manually actuated from outside of the housing 30 to enter data at the gas monitor station 14.

The keypad 206 is exposed to the environment around the gas monitor station 14. Therefore, depending upon the specific location where the gas monitor station 14 is positioned, the keypad 206 may be exposed to rain, sleet and/or snow. In addition, the data entry apparatus 5 will be exposed to hot summer sun and cold winter winds. Therefore, it is important that the data entry apparatus 5 be capable of withstanding a wide range of adverse environmental conditions.

In the embodiment of FIG. 7, the data entry apparatus 5 includes the keypad 206 which is manually actuated to enter data. However, it is contemplated that the data entry apparatus could have any one of many other known constructions. For example, the data entry apparatus 5 could include a plurality of switches which are contained within the housing 30 and are magnetically actuated from outside of the housing. Alternatively, a remote control unit, similar to the remote control units commonly utilized in association with television sets, could be utilized to actuate data entry apparatus contained within the housing 30.

A display 80 (FIGS. 7, 14 and 16) is provided in the housing 30. When the data entry apparatus 5 (FIGS. 7 and 14) is actuated to enter data at the gas monitor station 14 (FIG. 7), indicia at the display 80 changes to indicate the data entered. This enables an individual entering the data by manually actuating the keypad 206, to view the display 80 and determine whether or not the data was correctly entered. Of course, if the data was not correctly entered, the individual entering the data would actuate the keypad to revise the data. The display 80 also sets forth indicia which prompts an individual actuating the keypad 206 to enter the required data. The display 80 is effective to increase the user friendliness of the data entry apparatus 5 at the gas monitor station 14.

The keypad 206 is accessible from outside of the housing 30. The display 80 is visible from outside of the housing 30. This enables an individual desiring to enter data at the gas monitor station 14 to enter the data without opening the housing 30. However, if desired, the data entry apparatus 5 and/or display 80 could be enclosed within the housing. Of course, this would require an individual desiring to enter data at the gas monitor station 14 to open a cover or other part of the housing to obtain access to the data entry apparatus 5 and/or make the display 80 visible. Alternatively, the display 80 could be visible from outside of the housing and the data entry apparatus 5 enclosed within the housing. If this was done, a remote control apparatus, which may be similar to that utilized in association with a television set, may be used to effect the entry of data at the gas monitor station 14. Alternatively, while the housing 30 remains closed, one or more magnets outside of the housing could be utilized to actuate switches within the housing. By having the display 80 visible from outside the housing, an individual entering the data would be able to review the data. In addition, the individual would be able to follow instructions provided at the display 80 as to the next data to be entered.

A radio or transceiver 248 (FIGS. 8 and 14), corresponding to the transmitter 42 of FIG. 6, is enclosed within the housing 30. An antenna 26 is mounted on the outside of the housing 30. When a radio 248 (FIG. 8), disposed within the housing 30 is activated, radio signals are transmitted from the antenna 26 to the master station 18. These radio signals transmit data from the gas monitor station 40 to the master station 18.

The housing 30 (FIG. 8) includes a main section 212 and a cover section 214. When the housing 30 is in the closed condition illustrated in FIG. 7, the cover section 214 is fixedly connected to the main section 212 (FIG. 8) by suitable fasteners 216. Although the illustrated cover section 214 and main section 212 of the housing 30 are formed of aluminum, it is contemplated that the housing could be formed of other materials which would protect the contents of the housing from the environment around the gas monitor station 14. Of course, if the gas monitor station 14 is to be located within a building, rather than outside a building, the housing 30 would not have to be as rugged.

Figure 8:
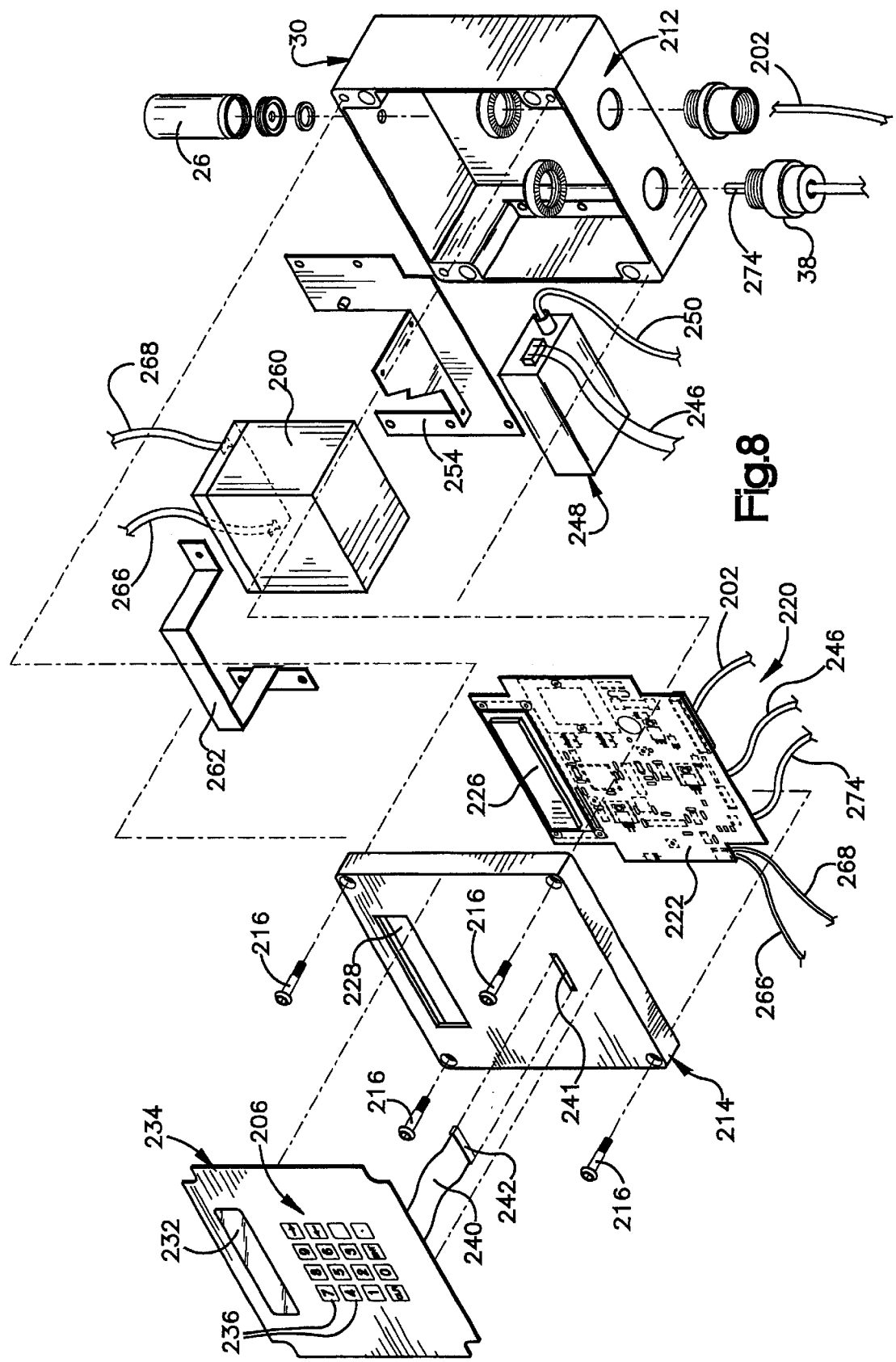
FIG. 8 is an exploded simplified illustration of apparatus utilized at the gas monitor station of FIG. 7 and illustrating a housing, data entry apparatus, control assembly, battery, radio, and sensor assembly which are disposed at the gas monitor station of FIG. 7.

The housing 30 encloses a control apparatus 220 (FIG. 8). In the illustrated embodiment, the control apparatus 220 includes a single printed circuit board 222 on which components of the control apparatus 220 are mounted. By mounting the components of the control apparatus 220 on a single circuit board, construction and/or maintenance of the control apparatus 220 is facilitated. The control apparatus 220 may include a plurality of circuit boards if desired.

The printed circuit board 222 (FIGS. 8, 9, 14 and 16) forms part of display 80 and is mounted on the inside of the cover section 214. A liquid crystal display 226 is mounted on the printed circuit board 222 (FIGS. 8 and 9) and is disposed in alignment with an opening 228 formed in the cover section 214 of the housing 30. A clear window 232 is disposed in a cover plate 234. It should be understood that the display 80 could have a construction other than the liquid crystal display 226.

The cover plate 234 has a multi-layered construction (FIG. 12) and includes a plurality of membrane switches (FIG. 11) disposed between layers of the cover plate. A suitable adhesive is provided on the back side of the cover plate 234 to fixedly secure the cover plate to the cover section 214 (FIG. 8). The adhesive on the back of the cover plate 234 secures the cover plate to the cover section 214 with the window 232 aligned with the opening 228 in the cover section 214. The cover plate 234 seals the opening 228 to prevent moisture from entering the housing 30.

Figure 11:
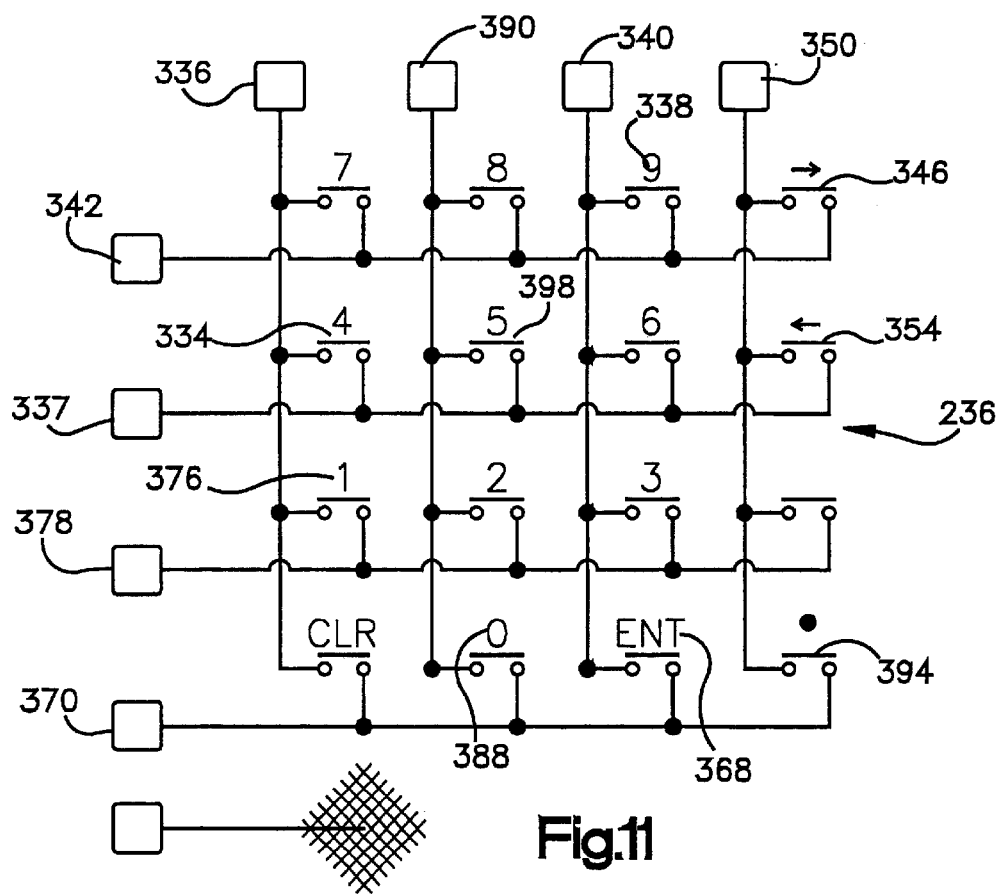
FIG. 11 is a schematic illustration depicting the relationship between manually actuated membrane switches in the data entry apparatus of FIG. 10.

A flexible conductor 240 (FIG. 8) extends from the cover plate 234 through a slot 241 in the cover section 214 to connector pins 243 (FIG. 18) on the printed circuit board 222 (FIG. 8) in the control apparatus 220. The flexible conductor 240 includes a plurality of flexible conductive ribbons which are connected with the membrane switches 236 (FIG. 11). The conductive ribbons extend from the membrane switches 236 to a connector 242 (FIG. 8) at one end of the conductor 240. The connector 242 is connected with the connector pins 243 (FIGS. 9 and 18) on printed circuit board 222 (FIGS. 8 and 9) of the control apparatus 220.

Figure 14:
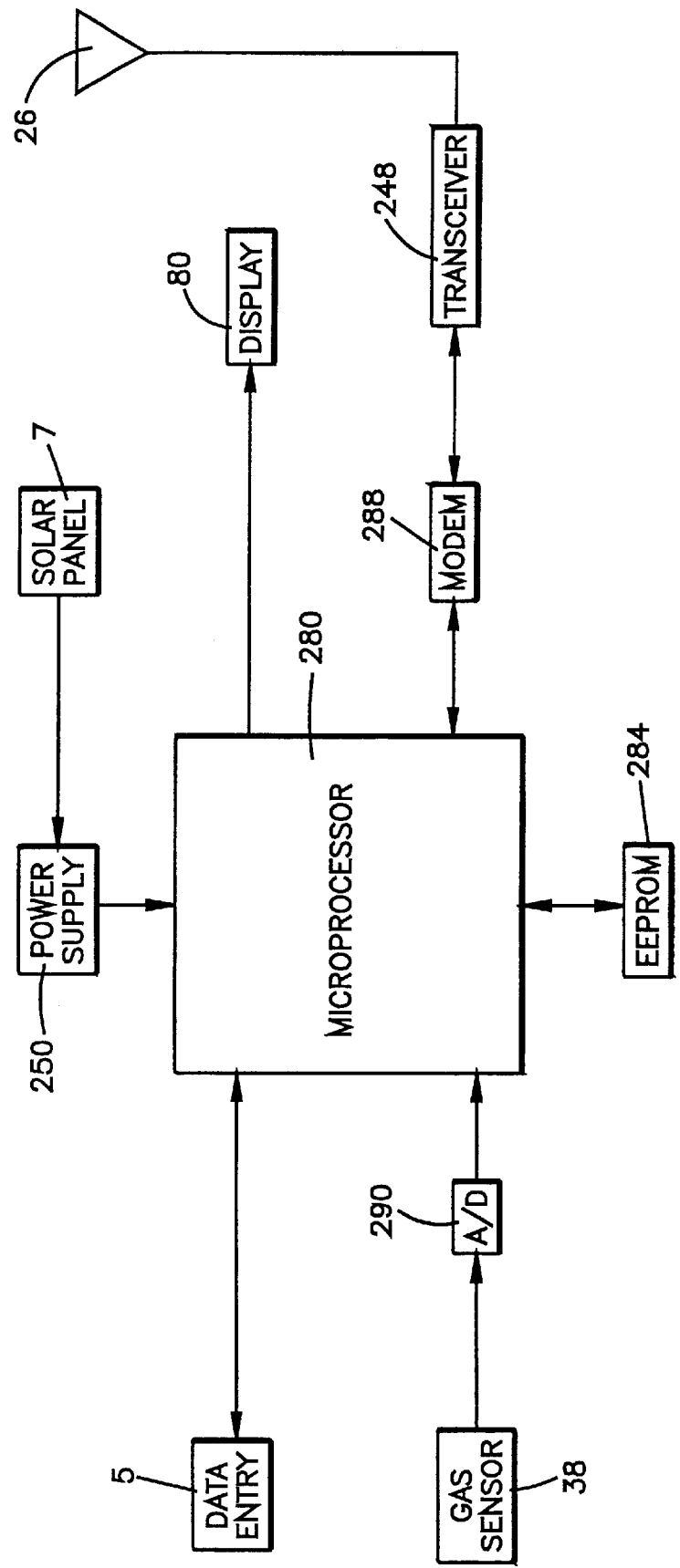
FIG. 14 is a schematic illustration depicting the relationship between components of the gas monitor station.
Figure 19:
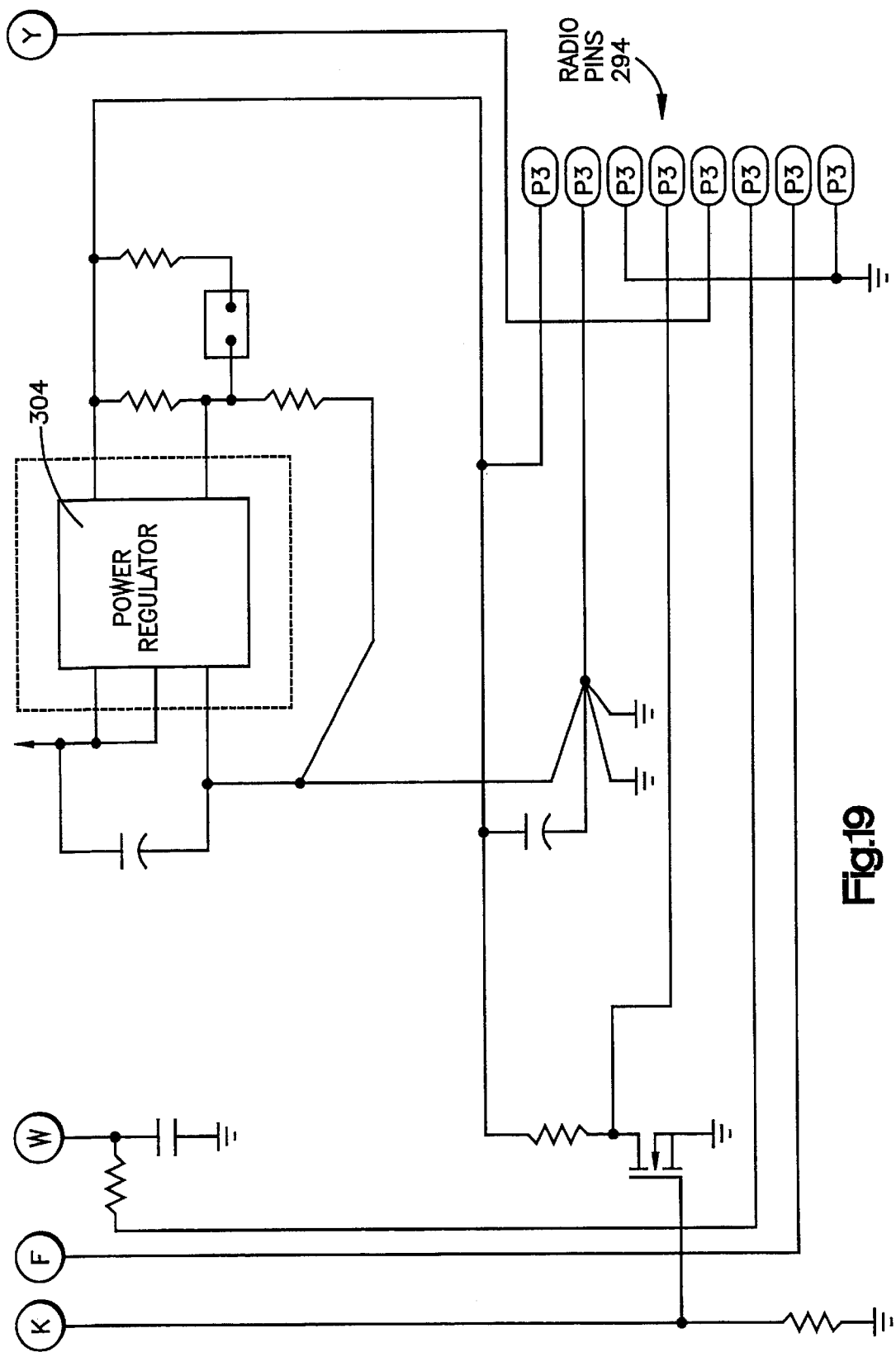
FIG. 19 is a schematic illustration of circuitry which connects a radio at the gas monitor station with the microprocessor of FIG. 16 and the modem of FIG. 18.

A radio cable 246 (FIG. 8) extends between a radio 248 (FIGS. 8 and 14) and the printed circuit board 222 of the control apparatus 220. The radio cable 246 is connected to the printed circuit board 222 at connectors 249 (FIG. 19). An antenna cable 250 (FIG. 8) extends between the radio 248 and the antenna 26 (FIGS. 7, 8 and 14). The radio or transceiver 248 (FIG. 8) can send signals to the master control station 18 and receive signals from the master control station. The radio or transceiver 248 performs the functions of the transmitter 42, transceiver 43, and receiver 44 of FIG. 6. The radio 248 is connected with a mounting bracket 254 (FIG. 8). The mounting bracket 254 is secured in the main section 212 of the housing 30 by suitable fasteners.

The control apparatus 220 is effective to control the operation of the radio or transceiver 248. Thus, when predetermined conditions, corresponding to data entered at the switches 236 of the keypad 206, have been met, the control apparatus 220 initiates transmission from the radio 248 to the master station 18. The master station 18 can initiate transmission to the radio 248.

Figure 15:
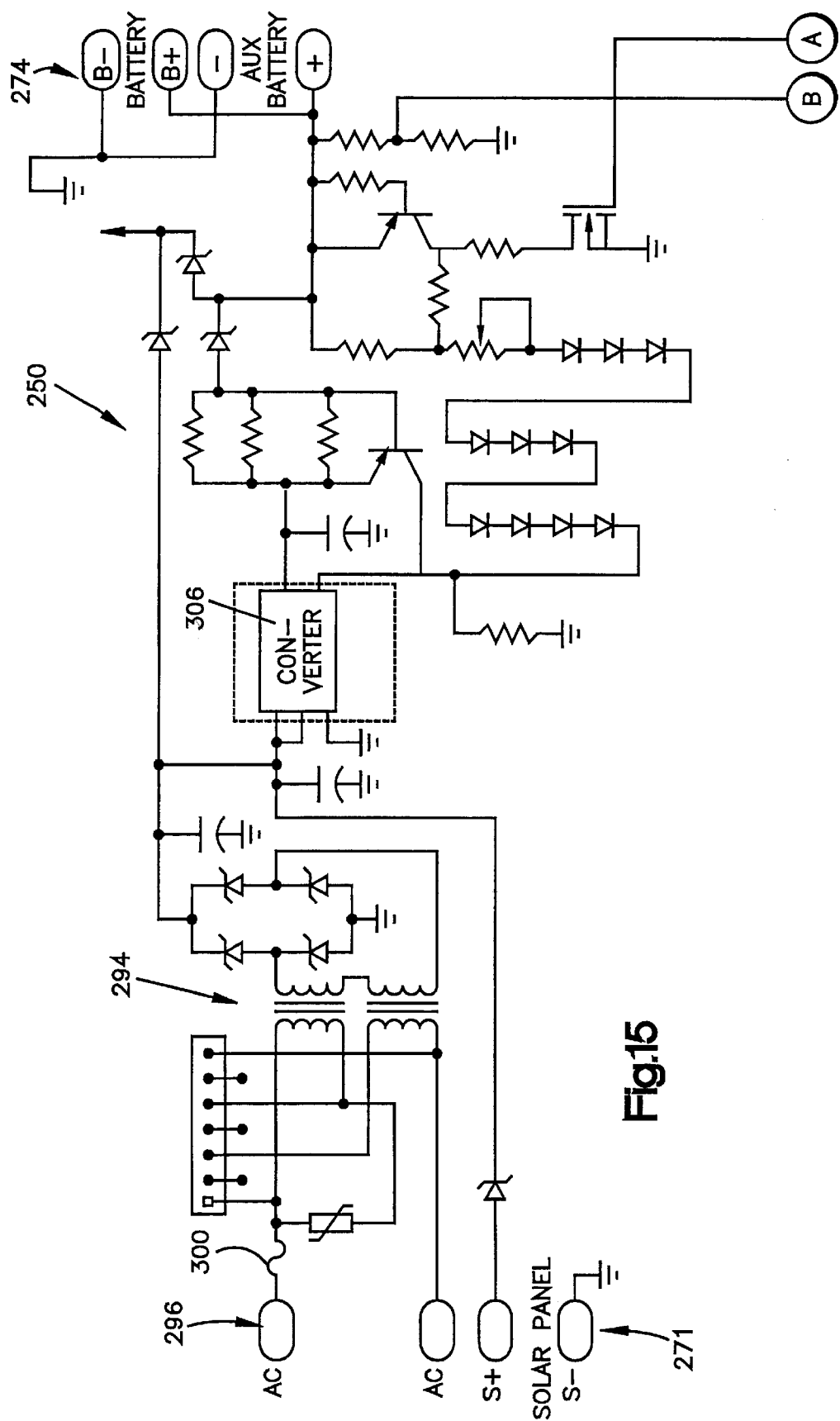
FIG. 15 is a schematic illustration of circuitry associated with power for the gas monitor station.

A power supply 250 (FIG. 14) includes a battery 260 (FIG. 8), corresponding to the battery 9 of FIG. 6, is secured to the mounting bracket 254 by a battery clamp 262. The battery 260 is connected with the printed circuit board 222 in the control apparatus 220 by a pair of conductors 266 and 268. The conductors 266 and 268 are connected with the printed circuit board 222 at terminals 274 (FIG. 15). The battery 260 provides power for the radio 248.

The solar panel 7 (FIG. 7) is connected with the printed circuit board 222 and the control apparatus 220 by the cable 202 (FIG. 8). The solar panel 202 is connected with the printed circuit board 222 at terminals 271 (FIG. 15). Power from the solar panel 7 charges the battery 260 in the power supply 250 (FIG. 14) to supplement the power provided by the battery. It is contemplated that other sources of power may be provided to supplement the battery 260 (FIG. 8) if desired. For example, a 110 volt, AC, power may be connected with a transformer 294 (FIG. 9) in the power supply 250.

Figure 17:
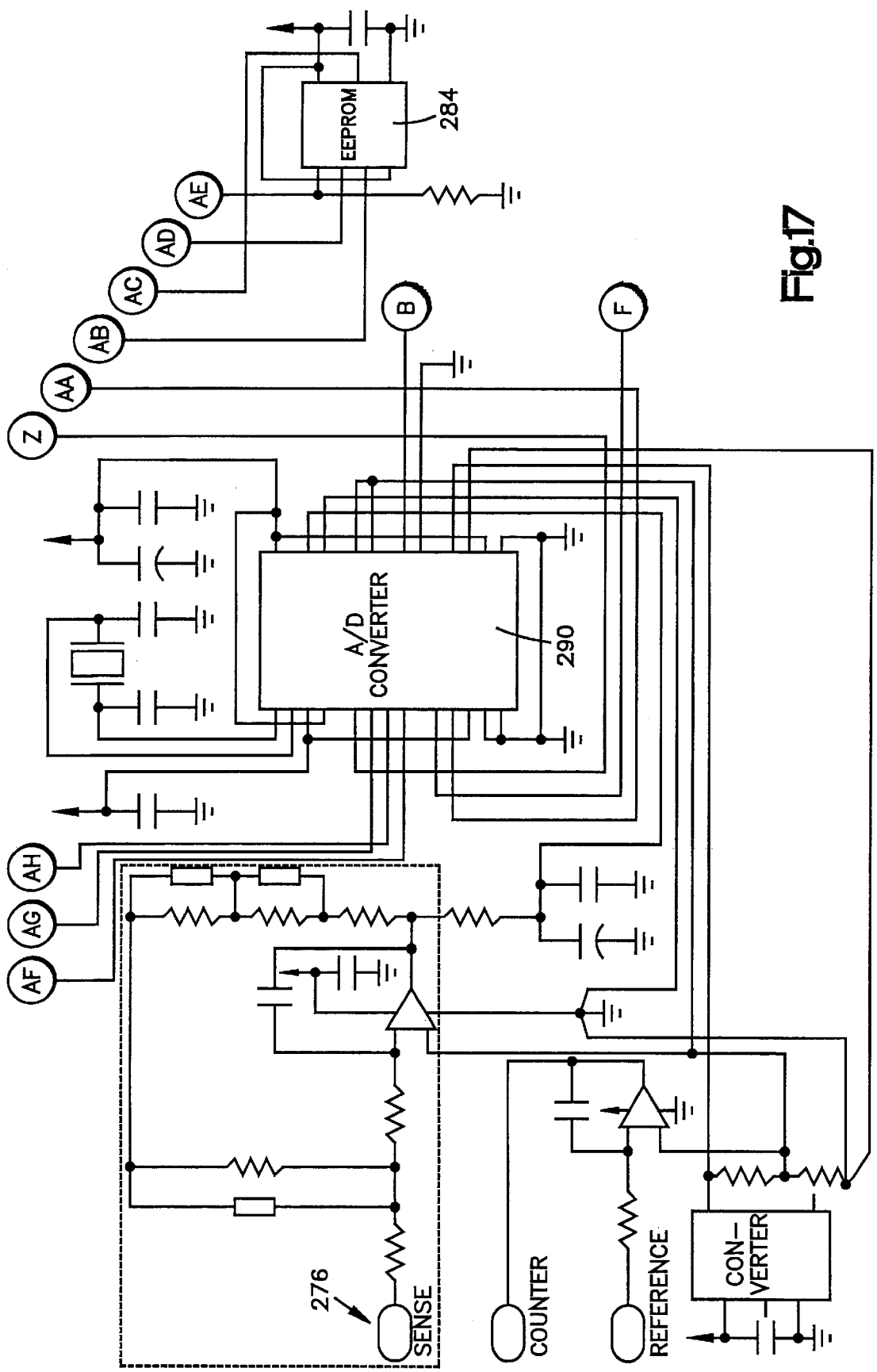
FIG. 17 is a schematic illustration of circuitry connected with a gas sensor at the gas monitor station and the microprocessor of FIG. 16.

The sensor 38 (FIGS. 7 and 14) is mounted on the outside of the main section 212 (FIG. 8) of the housing 30. The sensor 38 is connected with the control apparatus 220 by a sensor cable 274 (FIG. 8). The sensor cable 274 is connected with the printed circuit board 222 at terminals 276 (FIG. 17). The sensor 38 is an electrochemical sensor of the type which is commercially available from Sensoric, Inc. The sensor 38 may be of the aqueous or the organic non-aqueous type.

The sensor 38 may include a sensing electrode which is covered by a membrane of a suitable material, a counterelectrode, and a reference electrode. The selected gas to which the sensor 38 responds seeps through the membrane and reacts at the sensing electrode and/or electrolyte. Although the sensor 38 could have many different constructions, it is contemplated that the sensor could be constructed in a manner similar to that disclosed in U.S. Pat. Nos. 5,958,214; 5,538,620 or 6,129,825. It should be understood that the foregoing are merely examples of known sensors having operating principles which may be utilized in the sensor 38. It is contemplated that the sensor 38 could have any one of many different constructions.

Figure 9:
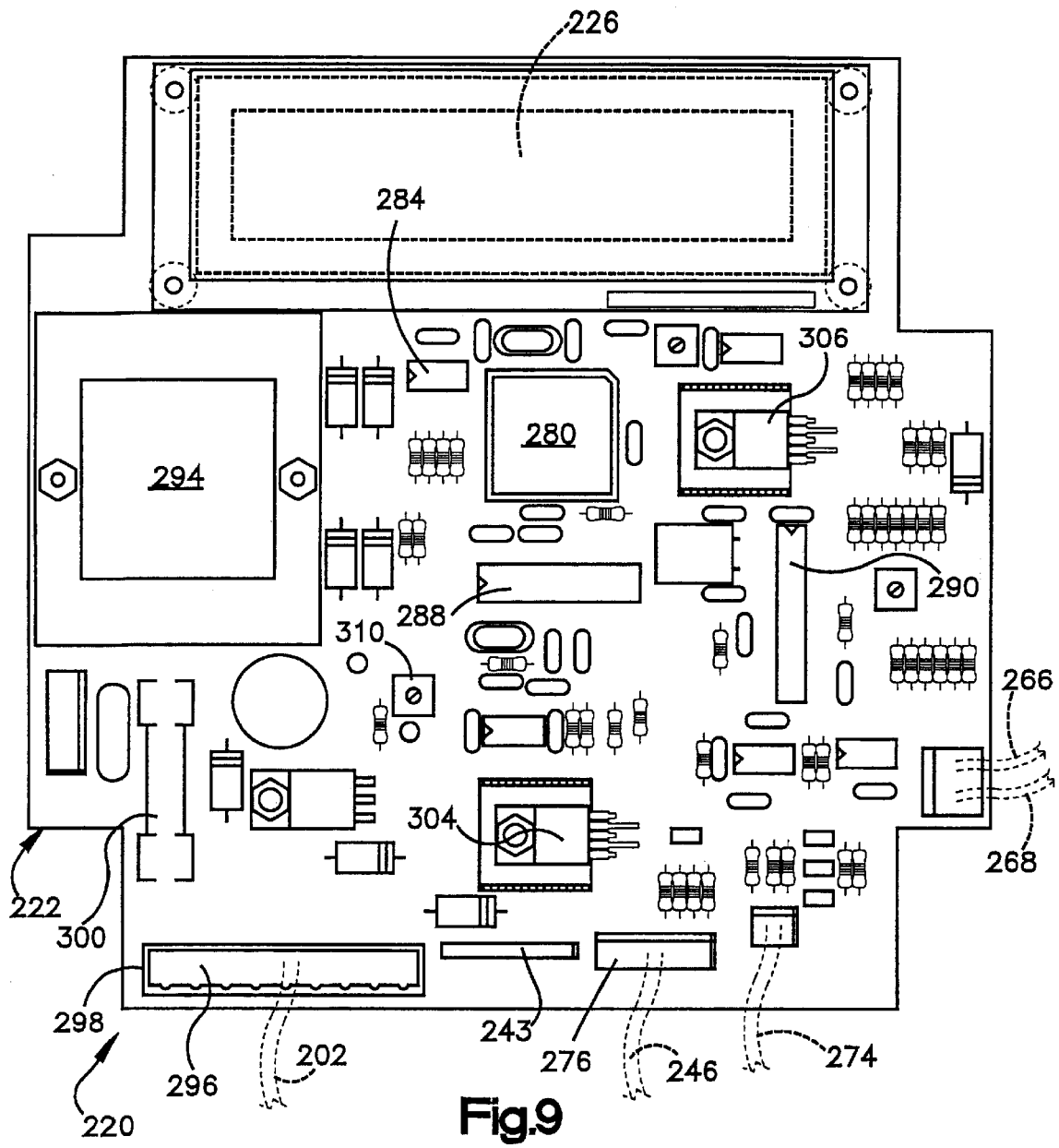
FIG. 9 is an enlarged simplified schematic illustration of the control assembly utilized at the gas monitor station of FIG. 7.
Figure 18:
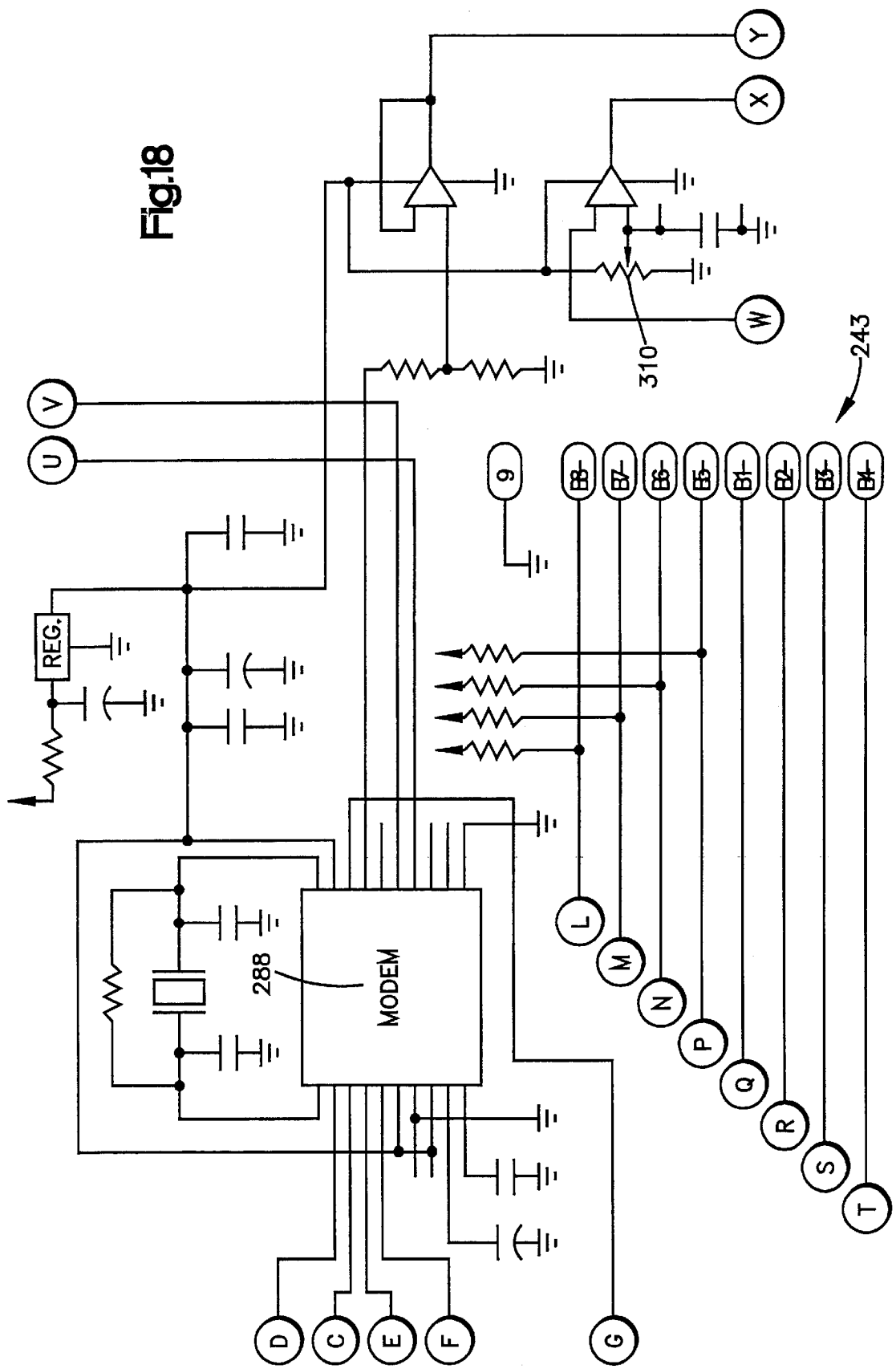
FIG. 18 is a schematic illustration of a modem and data entry circuitry connected with the microprocessor of FIG. 16.

The control apparatus 220 includes a microprocessor 280 (FIGS. 9, 14 and 16) which is mounted on the printed circuit board 222. The microprocessor 280 is connected with an EEPROM 284 (FIGS. 9 and 17) which functions as a storage bank for data transmitted to the microprocessor when the microprocessor is shut down. The flexible conductor 240 (FIG. 8) for the switches 236 in the keypad 206 is connected with the printed circuit board 222 at a connector 243 (FIGS. 9 and 18). This enables data input at the keypad 206 to be transmitted to the microprocessor 280.

A modem 288 (FIGS. 9, 14 and 18) is built onto the printed circuit board 222 and is connected with the microprocessor 280 (FIGS. 9, 14 and 16) and with the radio 248 (FIGS. 8 and 14) through the radio cable 246. When the microprocessor 280 makes a determination that predetermined conditions corresponding to data entered at the keypad 206 are present, the microprocessor initiates transmission with the radio 248 which is connected with the modem 288. The microprocessor 280 controls operation of the radio 248 in accordance with the data which is input at the keypad 206.

The sensor 38 (FIG. 8) is connected with the printed circuit board 222 by the sensor cable 274 (FIG. 9) at terminals 276 (FIG. 17). The sensor cable 274 is connected with the microprocessor 280 through an analog-to-digital converter 290 (FIGS. 9, 14 and 17). The sensor 38 may be specifically constructed to detect a selected gas.

The sensor 38 is effective to provide an analog output signal corresponding to the concentration of the selected gas in the atmosphere adjacent to the sensor. The output from the sensor 38 corresponding to the concentration of the selected gas in the atmosphere to which the sensor is exposed is transmitted through the cable 274 to the control apparatus 220. The cable 274 is connected with the analog-to-digital converter 290. The analog-to-digital converter 290 converts the analog output signal from the sensor 38 to a digital signal. The digital signal, corresponding to the analog output signal from the sensor 38, is transmitted to the microprocessor 280.

When the microprocessor 280 detects that a predetermined concentration of the selected gas is present in the atmosphere, the microprocessor initiates transmission by the radio 248 (FIGS. 8 and 14) to the master station 280. The specific control apparatus 220 illustrated in FIG. 9 is effective to transmit signals to the master station in response to detection of either one of two concentrations of the selected gas.

When the concentration of the selected gas reaches a first, relatively low, concentration, the microprocessor 280 initiates radio transmission of a HI signal to the master station 18. The HI signal indicates that the concentration of the selected gas has increased to a level which is of interest. When the concentration of the gas increases to a second level, the microprocessor 280 initiates transmission of a HIHI alarm signal with the radio 248. This HIHI alarm signal indicates to personnel at the master station 18 that the concentration of the selected gas in the atmosphere at the gas monitor station 14 has reached a level of concern and that suitable action should be taken.

Figure 16:
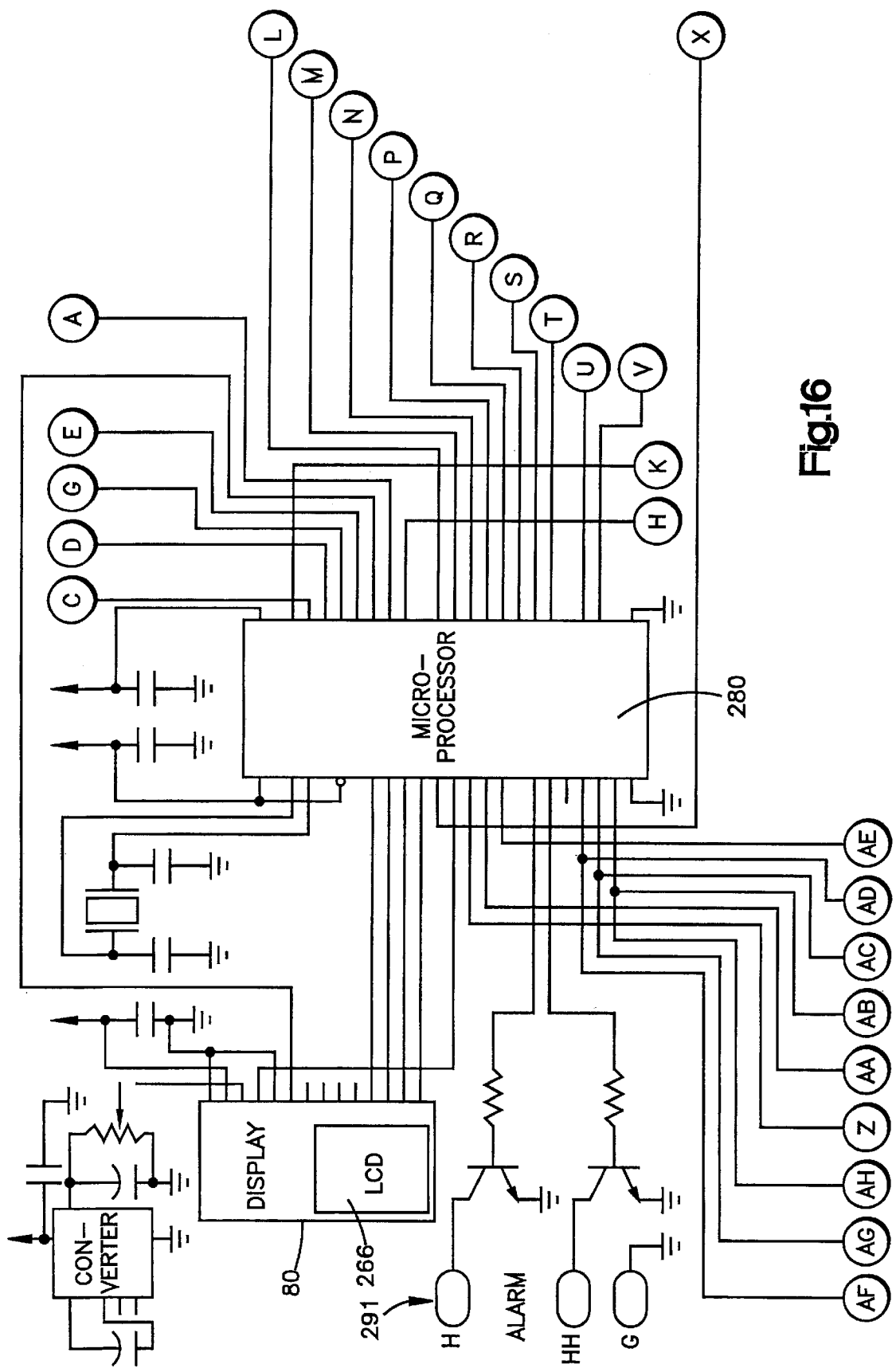
FIG. 16 is a schematic illustration of a microprocessor, display circuitry, and alarm circuitry which are connected with the circuitry of FIG. 15 at the gas monitor station.

In order to promote understanding of the situation by personnel at the master station 18, the radio 248 transmits data which is indicative of the actual concentration of the selected gas in the atmosphere adjacent to the gas monitor station 14. The data transmitted by the radio 248 to the master station 18 is displayed at the master station and indicates the actual concentration of the selected gas sensed by the sensor 38. Visual and/or audible alarms may be activated at the master station 18 when the data transmitted by the radio 248 corresponds to either a HI alarm or a HIHI alarm. Of course, visual and/or audible alarms may be provided when the data transmitted by the radio 248 corresponds to other predetermined conditions. In addition, visual and/or audible alarms may be provided at the gas monitor station 14. The alarms at the gas monitor station 14 may be connected with the printed circuit board 222 (FIGS. 8 and 9) at terminals 291 (FIG. 16).

It is contemplated that personnel at the master station 18 will want to know when there is a predetermined variation in the sensed quantity of the selected gas in the atmosphere at the gas monitor station 14. Therefore, the microprocessor 280 determines when the sensed concentration of the selected gas in the atmosphere adjacent to the gas monitor station 14 has either increased or decreased by a predetermined amount.

When the microprocessor 280 determines that the predetermined variation in the sensed concentration of the selected gas has occurred, the microprocessor initiates any alarm provided at the gas monitor station 14 and transmission to the master station with the radio 248. The microprocessor initiates transmission of a signal indicating the magnitude of the change in the concentration of the selected gas. The predetermined variation in concentration of the selected gas may occur when the concentration of the selected gas either increases or decreases by the predetermined amount.

It is contemplated that transient conditions may result in an instantaneous increase and/or decrease in the concentration of the selected gas in the environment around the gas monitor station 14. Thus, a relatively small puff of the selected gas may be blown past the gas sensor 38 (FIG. 7) at the gas monitor station 14. In order to prevent the transmission of data from the gas monitor station 14 to the master station 18 in response to these transient conditions or puffs of the selected gas, the microprocessor 280 is effective to average the input received from the sensor 38 over a predetermined period of time.

The period of time over which the microprocessor averages the input from the sensor 38 is relatively short to enable the control apparatus 220 to quickly respond to conditions which are not transient. Thus, the microprocessor 280 may average the input from the sensor 38 over a period of time of thirty seconds or less. For example, the microprocessor 280 may average the data received from the gas sensor 38 over a period of approximately ten seconds.

Before the microprocessor 280 initiates transmission with the radio 248 of an alarm signal, whether it is a HI signal or a HIHI signal to the master station, the level of concentration of the selected gas in the atmosphere adjacent to the gas monitor station will have been present for a short period of time, for example, ten seconds. By averaging the output from the gas sensor 38 over a short period of time, false or spurious alarms in response to transient conditions are avoided.

It is contemplated that it may be desired to have a short-term exposure limit (STEL) alarm. A short-term exposure limit alarm averages exposure level over a predetermined length of time. When a multiple of the average sensed concentration of the selected gas and the elapsed time over which the average sensed concentration is determined exceeds a predetermined magnitude, the microprocessor 280 initiates transmission with the radio 248 to inform the master station 18 that short term exposure limit has been exceeded.

For example, the average short-term exposure limit could be set for 0.3 parts per million (ppm) over a period of time, for example, fifteen minutes. The multiple of the average concentration of the selected gas (0.3 ppm) over the period of the selected time (15 minutes) is 4.5. Therefore, if there is an average exposure to 0.3 ppm of the selected gas for a period of fifteen minutes, the microprocessor 280 initiates transmission to the master station 18 with the radio 248.

It is contemplated that it will be desired to have some check at the master station 18 to determine whether or not the gas monitor station 14 is functioning. This is particularly true when the circumstances are such that the microprocessor 280 does not initiate transmission with the radio 248 in response to a change in sensed concentrations of the selected gas or a change in status for a long period of time. Therefore, when the microprocessor 280 determines that a predetermined maximum length of time has elapsed since the last transmission was made with the radio 248, the microprocessor initiates transmission with the radio 248 to the master station 18.

For example, if a time period of thirty minutes passes after a transmission is made by the radio 248 to the master station, the microprocessor 280 initiates transmission with the radio to the master station. This informs the master station 18 that the gas monitor station 14 is still functioning. The master station then resets a timer for the maximum length of time between communications from the gas monitor station 14.

If more than the predetermined time period, for example, sixty-five minutes, passes between communications from the gas monitor station 14 to the master station 18, an alarm is provided at the master station. This alarm indicates to personnel at the master station that the gas monitor station 14 has not transmitted to the master station for more than the predetermined period of time. Personnel at the master station 18 can then initiate an inspection of the gas monitor station 14 to determine why the gas monitor station 14 had not transmitted to the master station for more than the predetermined period of time.

The microprocessor 280 is also effective to determine when the power level, that is the output voltage, from the battery 260 is below a predetermined level. Thus, the output voltage of the battery 260 is transmitted to the control apparatus 220 through the conductors 266 and 268 (FIGS. 8 and 9). The microprocessor 280 (FIG. 9) receives an input indicative of the output voltage of the battery 260. When this output voltage falls below a predetermined level, for example, 12 volts (direct current), the microprocessor 280 initiates a transmission with the radio 248 to the master station 18 to indicate that the output of the battery is below a desired level. When they are not being used, the microprocessor 280 and radio 248 are shut down to a de-powered or standby condition to minimize the load on the battery 260.

The microprocessor 280 also initiates a transmission with the radio 248 to the master station 18 if the output from the battery changes by more than a predetermined amount. For example, if the battery voltage should increase or decrease by more than 0.5 volts within the predetermined period of time, the microprocessor 280 would initiate transmission with the radio 248 to indicate to the master station that there has been a change in battery voltage.

It should be understood that when the microprocessor 280 initiates transmission with the radio 248 to the master station 18, the radio is effective to transmit data indicative of the condition which is present. For example, when the sensed concentration of the selected gas in the atmosphere at the gas monitor station 14 exceeds a concentration necessary to trigger the HI alarm, the microprocessor 280 initiates transmission with the radio 248 to transmit data indicative of the actual sensed concentration of the gas in the environment adjacent to the gas monitor station. Similarly, when the concentration of the selected gas in the environment adjacent to the gas monitor station 14 reaches a level sufficient to trigger a HIHI alarm, the radio 248 transmits data indicative of the actual concentration of the selected gas in the atmosphere. When the microprocessor 280 initiates operation of the radio 248 in response to a predetermined variation in the concentration of the selected gas in the atmosphere at the gas monitor station 14, data indicative of the actual concentration of the selected gas and the actual variation in the concentration of the selected gas is transmitted from the gas monitor station to the master station by the radio 248.

In addition to the microprocessor 280, the control apparatus 220 includes other components including a transformer 294 (FIGS. 9 and 15). The transformer 294 forms part of the power supply 250 (FIG. 14). The transformer 294 may be connected with a source of alternating current, such as a 110 volt power line. The alternating current is connected with the printed circuit board 222 at connection locations indicated by the numeral 296 (FIGS. 9 and 19) on a terminal block 298 (FIG. 9). The transformer 294 is connected with the connection locations 296 through a suitable fuse 300 (FIGS. 9 and 15). The transformer 294 transforms either 115 volt or 230 volt line current to a relatively low level (approximately 13 or 14 volts) required to charge the battery 260.

In addition to the transformer 294 (FIG. 9), the control apparatus 220 includes a radio power regulator 304 (FIGS. 9 and 19) which is mounted on the printed circuit board 222 and connected with the radio 248. A solar panel regulator or voltage converter 306 (FIGS. 9 and 15) is also provided on the circuit board 222 in the control apparatus 220. A radio squelch setting potentiometer 310 (FIGS. 9 and 18) is provided on the circuit board 222 in the control apparatus 220.

Figure 10:
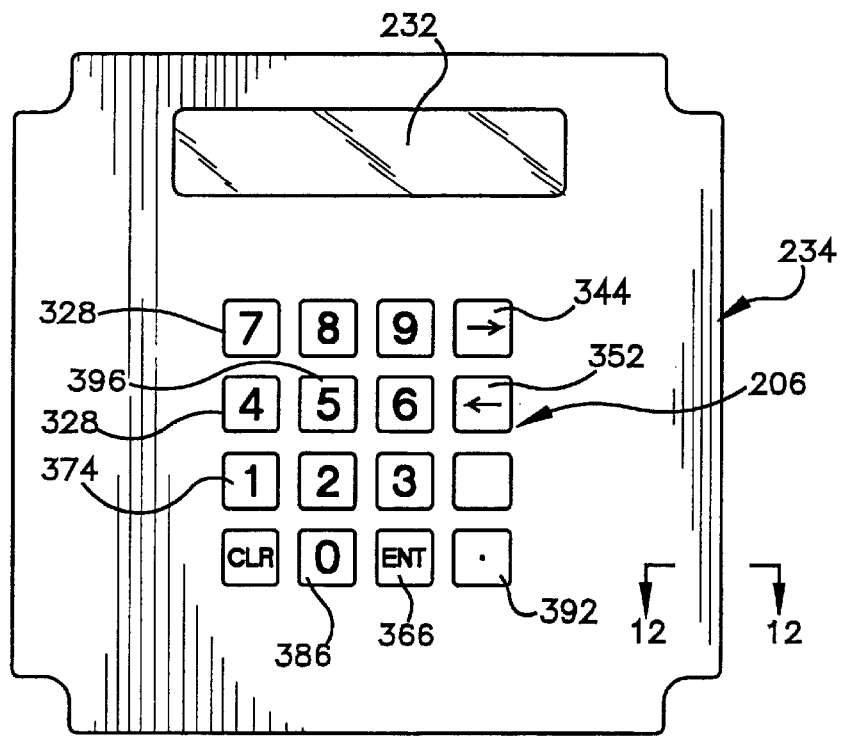
FIG. 10 is a simplified plan view of data entry apparatus and a display provided at the gas monitor station of FIG. 7.
Figure 12:
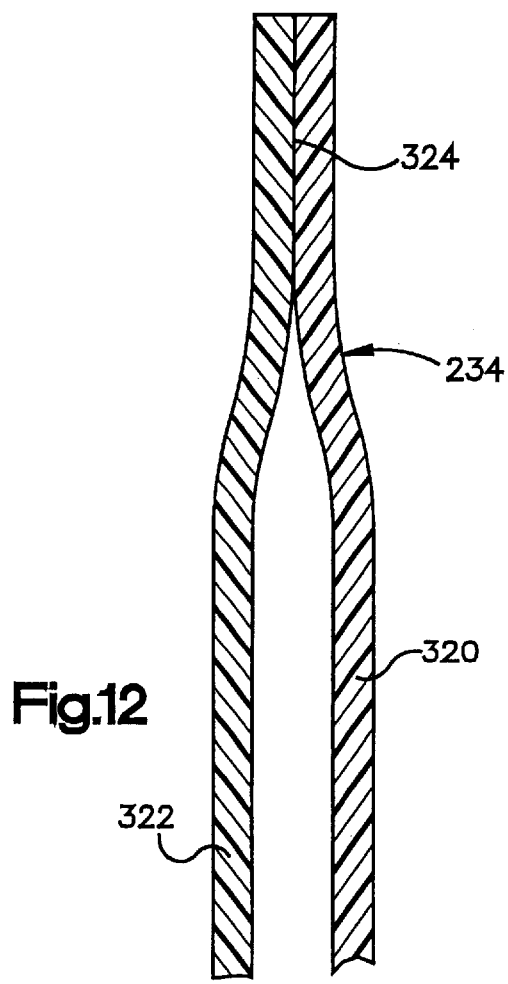
FIG. 12 is an enlarged fragmentary schematic sectional illustration, taken along the line 12—12 of FIG. 10, illustrating the construction of a portion of an enclosure for the switches of FIG. 11.

The construction of the cover plate 234 is illustrated in FIGS. 10 and 12. As was previously mentioned, the cover plate 234 has a multi-layered construction. A front layer 320 (FIG. 12) of the cover plate 234 is connected with a rear layer 322 at a sealed connection 324. The sealed connection 324 is formed by heat and a polyester base dry film adhesive. The connection 324 is free of pressure sensitive adhesive which tends to lose its adhesive properties when exposed to heat provided by the sun.

The sealed connection 324 extends completely around the periphery of the cover plate 234 and securely seals membrane switches 236 disposed within the cover plate 234 from the environment around the cover plate. The cover plate 324 has a known construction and is commercially available from Berquist Company. However, it should be understood that the cover plate 234 could have different construction if desired.

Membrane switches 236 (FIG. 11) are provided between the front and rear layers 320 and 322 of the cover plate 234. The front layer 320 forms a continuous layer which extends across the entire front of the cover plate 234, with the exception of the window 232. The window 232 is formed of a clear plastic or other transparent material. The front and rear layers 320 and 322 are sealed around the periphery of the window so that liquid, cannot seep into the space between the front layer 320 and rear layer 322 of the cover plate 234.

The front layer 320 of the cover plate is provided with indicia 328 (FIG. 10) which overlies the membrane switches 236 (FIG. 11). By manually pressing against the indicia 328 on the front layer 320 of the cover plate 234, the corresponding membrane switch is actuated. Thus, by pressing on indicia indicative of the numeral "4", a membrane switch 334 (FIG. 11) corresponding to the numeral 4 and disposed between the rear layer 322 and front layer 320 is actuated.

The relationship between the various switches which form the keypad 206 is illustrated schematically in FIG. 11. For example, if the indicia 328 indicated by the numeral "4" in FIG. 10 is manually depressed, the switch indicated at 334 is actuated. Actuation of the switch 334 completes a circuit between a terminal pin 336 and a terminal pin 337. Completing the circuit between the terminal pins 336 and 337 indicates to the microprocessor 280 that the indicia 328 for the numeral "4" on the keypad 206 was manually actuated. The microprocessor 280 then effects the transmission to the liquid crystal display 226 (FIG. 9) to have the numeral "4" appear in the display at the window 232 (FIG. 10).

Similarly, if the indicia 328 corresponding to the numeral "9" is manually actuated on the keypad 206, a switch 338 (FIG. 11) is closed to complete a circuit between a terminal pin 340 and a terminal pin 342. The microprocessor 280 will then cause the numeral "9" to appear on the display 226. By having the display 226 set forth the indicia which is actuated on the keypad 206, a person actuating the keypad can manually view the display through the window 232 and check the data which has been entered.

By depressing right arrow indicia 344 on the keypad 206, a switch 346 (FIG. 11) is closed. The resulting completion of a circuit between the terminal pin 342 and a terminal pin 350 indicates to the microprocessor 280 that the menu which prompts the individual entering data should be advanced. Similarly, depressing left arrow indicia 352 on the keypad 206 results in actuation of a switch 354 (FIG. 11). Depressing of the switch 354 completes a circuit between the terminal pin 350 and the terminal pin 337. This indicates to the microprocessor 280 that the menu provided on the liquid crystal display 226 should be scrolled backward to enable the operator to enter data which had previously been missed or to revise data which had previously been entered.

When the gas monitor station 14 (FIG. 7) is to be utilized to sense a selected gas, a gas sensor 38 which is capable of sensing the selected gas is connected with the sensor cable 274 (FIG. 8). This connects the gas sensor 38 with the control apparatus 220. The sensor for the selected gas is connected to the housing 30 in the manner illustrated in FIG. 7. The selected gas may be any one of the gases previously mentioned herein.

The keypad 206 (FIGS. 8 and 10) is then actuated to transmit data to the microprocessor 280 (FIG. 8) indicative of the selected gas. As was previously mentioned, the gas sensor 38 may be constructed to sense any one of many different gases. Of course, the keypad 206 would be manually actuated to transmit data to the microprocessor 280 indicative of the selected gas.

The gas sensor 38 may then be calibrated. The sensor 38 is calibrated by exposing the sensor to a known concentration of the selected gas. This may be done by exposing the sensor 38 to the interior of a container containing a known concentration of the selected gas. Rather than being exposed to a container containing a known concentration of the selected gas, the sensor 38 could be exposed to a gas-generating device, such as a permeation tube calibrator or gas generator. The output of the sensor 38 in response to exposure to the known concentration of the selected gas is transmitted to the analog-to-digital converter 290 (FIGS. 9 and 17) in the control apparatus 220. The analog-to-digital converter 290 converts the analog output of the gas sensor 38 to a digital signal which is transmitted to the microprocessor 280.

A number corresponding to the output of the gas sensor 38 is then displayed on the liquid crystal display 226. The number corresponding to the output of the gas sensor 38 can be viewed through the window 232 (FIG. 10) by the individual operating the keypad 206 (FIG. 7). The individual operating the keypad 206 then actuates the indicia 328 (FIG. 10) to close switches 236 (FIG. 11) corresponding to the known concentration of the selected gas in the container.

This results in the transmission of data to the microprocessor 280 (FIG. 9) indicating a gas concentration corresponding to the known concentration of the selected gas to which the sensor 38 is exposed. When this has been done, the microprocessor 280 is calibrated so that it will effect actuation of the display 226 to indicate the known gas concentration to which the sensor 38 is exposed. In addition, when the microprocessor 280 initiates operation of the radio 248 to transmit to the master station, the microprocessor will cause the radio to transmit data corresponding to the sensed gas concentration of the selected gas to the master station 18. Calibration data stored in the microprocessor 280 (FIGS. 9 and 16) is transmitted to the EEPROM 284 (FIGS. 9 and 17) when the microprocessor is shut down, that is, de-powered.

The illustrated gas sensor 38 has a hose barb 360 (FIG. 7) which connects a hose extending from a container of known concentration of the selected gas, to the sensor 38. Once the control apparatus 220 has been calibrated, is the hose and container of known concentration of the selected gas are disconnected from the hose barb 360 on the gas sensor 38. Of course, the container of a known concentration of the selected gas could be connected with the gas sensor 38 in a different manner if desired. It should be understood that the gas sensor 38 could be exposed to a known concentration of the selected gas in any one of many different ways.

When the gas monitor station 14 is to be configured to initiate radio transmission in response to the occurrence of predetermined conditions, an individual at the gas monitor station 14 manually depresses "ENT" indicia 366 on the keypad 206 (FIG. 10). Manually depressing the indicia 366 actuates an "ENT" switch 368 (FIG. 11). Actuation of the "ENT" switch 368 connects terminal pin 340 with a terminal pin 370. This causes the microprocessor 280 to change the liquid crystal display 226 (FIG. 9) to indicate either option "1 SUPERVISOR" or option "2 USER". The Supervisor can change all of the parameters of the gas monitor station 14 while the User can only zero and span the sensor.

Since the gas monitor station 14 is being configured to set the conditions which result in initiation of radio transmission, the individual actuating the keypad 206 will be a Supervisor and will select option "1 SUPERVISOR". This will be accomplished by depressing the indicia 374 on the keypad 206 (FIG. 10). Actuation of the indicia 374 results in the switch 376 (FIG. 11) being closed to complete a circuit between the terminal pin 336 and a terminal pin 378.

This indicates to the microprocessor 280 that a Supervisor's security code is to be entered next. Therefore, the microprocessor 280 changes the display 226 to request entry of the Supervisor's security code. The Supervisor actuates the indicia 328 on the keypad 206 to enter the security code. The security code may be a four-digit number, such as 1234. The "ENT" (enter) indicia 366 is then actuated to close the switch 368 to input the security code to the microprocessor 280.

By pressing a right arrow indicia 344, the right arrow switch 346 is closed and request for the settings for the battery alarm and a battery dead band will appear at the display window 232. The keypad 206 will then be actuated to enter the battery output voltage at which the microprocessor 280 will initiate operation of the radio 248 to transmit a battery alarm to the master station. Usually, the battery alarm voltage is set at 12 VDC. However, it should be understood that a different voltage could be utilized if desired.

The battery dead band voltage is the amount by which the output of the battery 260 must change to cause the microprocessor 280 to initiate transmission by the radio 248 to the master station informing the master station of the change in battery output voltage. The battery dead band setting is entered into the microprocessor 280 by actuating the keypad 206.

It is contemplated that the battery dead band may be set at 0.5 volts. This will be accomplished by manually actuating indicia 386 (FIG. 10) for the numeral zero (0). This will result in an actuation of a switch 388 to complete a circuit between a terminal pin 390 and the terminal pin 370. The decimal point (.) is entered by actuating indicia 392 (FIG. 10) on the keypad 206. This results in actuation of a switch 394 to complete a circuit between terminal pins 350 and 370. Indicia 396 (FIG. 10) on the keypad 206 for the numeral five (5) is then manually actuated to close a switch 398. Closing of the switch 398 completes a circuit between the terminal pins 337 and 390.

Once the battery alarm and battery dead band settings have been entered into the microprocessor 280 (FIG. 9), the right arrow indicia 344 (FIG. 10) is again manually depressed. This results in closing of the switch 346 (FIG. 11) and a change in the display at the window 232. The display at the window 232 will then request settings for the sensor type and analog filter. Indicia 328 corresponding to a numerical code for the selected gas sensor 38 is then actuated. This results in the inputting of data to the microprocessor 280 indicating the type of sensor 38 which is being used and the selected gas which is to be sensed by the sensor. The data indicating the type of sensor 38 which is being used is stored in the EEPROM 284 when the microprocessor 280 is shut down.

An analog filter setting is then entered into the microprocessor 280. The analog filter setting corresponds to a period of time over which readings by the sensor 38 are to be averaged. The period of time over which readings by the sensor are averaged is relatively short, for example, thirty seconds or less.

By averaging the output of the sensor 38 over a period of time, the effect of transient conditions, such as puffs of the selected gas, are eliminated. If the output from the sensor 38 was not averaged over a short period of time in order to eliminate the effect of transient conditions, it is possible that numerous nuisance or false alarms could be provided as a result of short duration variations in the amount of the selected gas which is immediately adjacent to the sensor 38 at any given instance. In one specific configuration of the gas monitor station 14, the keypad 206 was actuated to indicate that the analog filter or averaging time was to be ten seconds. Data corresponding to the analog filter averaging time is stored in the EEPROM 284 when the microprocessor 280 is shut down.

Once the sensor type and analog filter time has been entered by actuating the keypad 206, the right arrow indicia 344 is again actuated. This results in the microprocessor 280 (FIG. 9) changing the display 226 to request a STEL (short term exposure limit) setting and a Gas Dead Band setting. The short-term exposure limit (STEL) setting is a number which corresponds to the maximum permissible moving average concentration of gas over a predetermined length of time.

Figure 13:
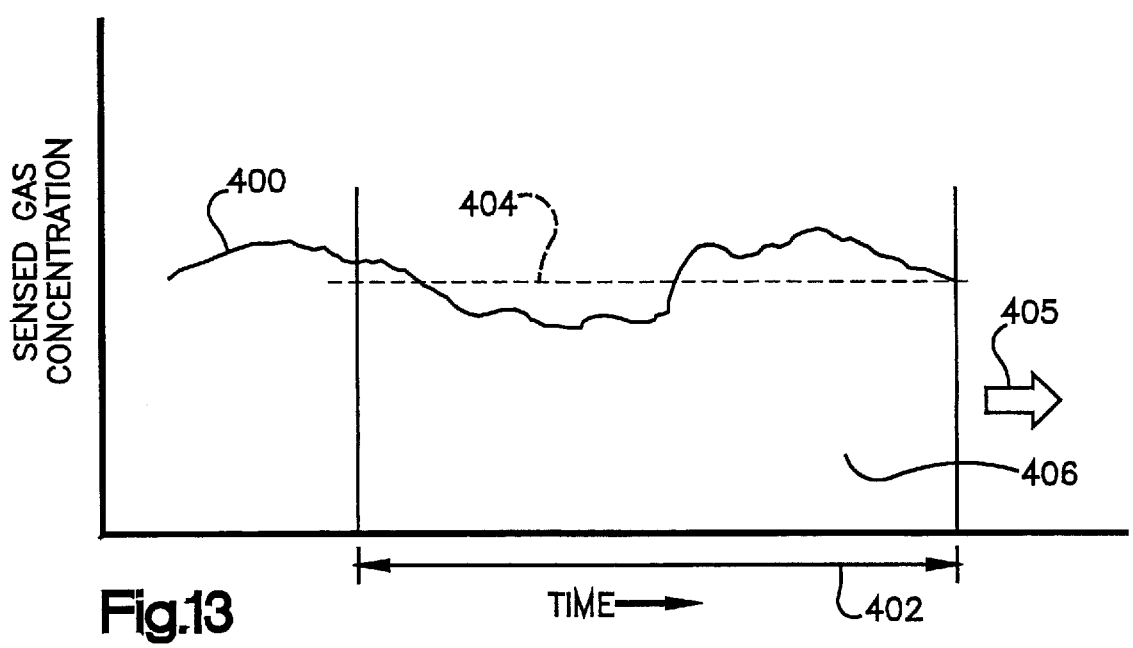
FIG. 13 is a graph depicting the manner in which sensed gas concentration varies as a function of time.

The manner in which sensed gas concentration in the atmosphere at the gas monitor station 14 may vary is illustrated by a curve 400 in FIG. 13. A predetermined length of time over which the moving average gas concentration is determined is represented by a line 402 in FIG. 13. The line 402 extends from the present time back for a predetermined amount of time, for example fifteen minutes. The moving average gas concentration is represented by the dashed line 404 in FIG. 13.

The line 402 representing the predetermined length of time over which the average gas concentration is determined continuously moves to the right, as viewed in FIG. 13, with the passage of time. This rightward movement of the time line 402 is indicated by an arrow 405 in FIG. 3. Therefore, the moving average gas concentration represented by the line 404 may be referred to as a sliding or rolling average.

The moving average gas concentration 404 may be multiplied by the predetermined length of time 402 over which the moving average is determined. This results in a number having a magnitude which corresponds to an area 406 under the curve 400 in the predetermined length of time 402. The area 406 is the moving integral of gas concentration. Since the predetermined length of time 402 is a constant, the multiple of the moving average gas concentration 404 times the predetermined length of time 402 is equal to a constant times the moving average gas concentration.

By setting a short-term exposure limit alarm which is a function of both the duration of exposure to the selected gas and the concentration of the selected gas, an alarm is provided when the short-term exposure is relatively high. The microprocessor 280 provides a continuous series of sensing periods for which the multiple of elapsed time in the sensing period and sensed concentration of the selected gas is continuously determined by the microprocessor. The microprocessor 280 continuously determines the moving average gas concentration 404 over the predetermined length of time 402. If the moving average gas concentration exceeds a predetermined number, the microprocessor 280 initiates transmission to the master station 18 with the radio 248.

In one specific embodiment of the invention, a permissible short-term exposure number equal to the area 406 (FIG. 13) was entered into the microprocessor 280. The actual short-term exposure number determined by the microprocessor 280 was continuously compared to a permissible short-term exposure limit number. The permissible short-term exposure limit number for one selected gas was, for example, determined by operating personnel to be 4.5. When the microprocessor 280 is shut down, the short-term exposure number is stored in the EEPROM 284.

The permissible short-term exposure limit number of the foregoing example, that is, 4.5, was transmitted to the microprocessor 280 (FIG. 9) by actuating the indicia 328 (FIG. 10) for the numeral 4 with a resulting closing of the switch 334 (FIG. 11). This completes the circuit between the terminal pins 336 and 337. The indicia for the decimal point, that is, the indicia 392 (FIG. 10), on the keypad 206 is then manually actuated. This results in closing of the switch 394 (FIG. 11) to complete a circuit between the terminal pins 350 and 370. The indicia 396 for the numeral would then be manually depressed. This would result in closing of the switch 398 and a completion of the circuit between the terminal pins 390 and 337. This results in the inputting to the microprocessor 280 of a short-term exposure limit number of 4.5.

The duration of the sensing periods over which the moving average gas concentration for the short-term exposure limit is measured may also be entered into the microprocessor 280 from the keypad 206. Thus, in one specific instance, the measuring period 402 for the short-term exposure limit was fifteen minutes. The measuring or sensing period 402 could have a duration either longer or shorter than fifteen minutes if desired. This data is also stored in the EEPROM 284 when the microprocessor 280 is shut down.

Once the data entry has been completed and the predetermined permissible short term exposure limit has been entered into the microprocessor 280, the microprocessor will initiate transmission of an alarm to the master station 18 whenever the predetermined multiple of the time 402 and the moving average gas concentration 404 is reached. In the previous example, a multiple of 4.5 was input to the microprocessor as the permissible short-term exposure limit number. Thus, if there is a moving average sensed gas concentration 404 of 0.3 parts per million (ppm) for the measuring period 402 of fifteen minutes, the short exposure limit multiple would be 4.5. This would be equal to the permissible short-term exposure limit number and would result in the microprocessor 280 initiating radio transmission of an alarm to the master station 18 with the radio 248.

Rather than entering a permissible short term exposure limit number corresponding to the area 406, the permissible short term exposure limit number could correspond to the moving average gas concentration represented by the dashed line 404 in FIG. 13. In the foregoing example, the permissible moving average gas concentration was 0.3 parts per million over a predetermined length of time 402 of fifteen minutes. Rather than entering the selected short-term exposure number of 4.5, the moving average gas concentration number of 0.3 parts per million over the predetermined length of time 402 could be entered.

During determination of the moving average gas concentration 404, the analog filter time is in effect. This means that readings by the gas sensor 38 are averaged over a short period of time to determine the curve 400 and the moving average gas concentration 404. As was previously mentioned, the analog filter time is relatively short, thirty seconds or less. In the previous example, the analog filer time was selected to be ten seconds.

The previous examples of analog filter time of ten seconds and a length of time 402 (FIG. 13) over which the moving average gas concentration 404 is determined of fifteen minutes are assumed to have been entered into the microprocessor 280 at the keypad 206. The moving average gas concentration 404 would then be determined based on ninety gas concentration values. This is because there would be six average analog filter gas concentration values determined over ten second time averaging periods in one minute. In the fifteen minute length of time 402, over which the moving average gas concentration 404 is determined, there would be a determination of six times fifteen or ninety gas concentration values.

It should be understood that the analog filter time for averaging readings by the sensor 38 could be different than the foregoing example of ten seconds. Similarly, the length of time 402 over which the moving average gas concentration is determined could be different than the foregoing example of fifteen minutes.

If desired, the short-term exposure limit could be determined without the analog filter to average output readings from the sensor 38. Alternatively, the analog filter could be used to average output readings from the sensor 38 without utilization of the short-term exposure limit setting. It is contemplated that the short-term exposure limit could be used without the analog filter while the analog filter is used for other purposes. For example, the analog filter could be used for averaging of reading of the sensor 38 over a short length of time, that is, thirty seconds or less, to determine whether or not a predetermined level of concentration of the selected gas is present in the atmosphere at the gas monitor station. At the same time, the short-term exposure limit could be determined by obtaining the moving average 404 of the unfiltered output of the sensor 38 over the predetermined period of time 402.

The magnitude of a gas dead band is then transmitted from the keypad 206 to the microprocessor 280. The gas dead band is the amount of change in the output of the sensor 38 which is required to cause the microprocessor 280 to initiate radio transmission of data to the master station. For example, the gas dead band could be set to be a variation of 0.1 parts per million (ppm) in the concentration of the selected gas. If this was done, the microprocessor 280 would initiate radio transmission of data to the master station whenever the amount of the selected gas in the atmosphere changed by more than 0.1 parts per million. The required variation in the amount of the selected gas in the atmosphere to initiate transmission by the radio 240 may be either an increase or a decrease in the concentration of the selected gas.

The settings for the HI alarm and the HIHI alarm are then input from the keypad 206 to the microprocessor 280. The HI alarm is a relatively low setting, for example, 1.0 parts per million of the selected gas, while the HIHI alarm is a higher concentration of the selected gas, for example, 2.0 parts per million. The HI alarm is set at a gas concentration level which initiates investigative action on a non-urgent basis. However, the HIHI alarm would initiate investigation on an urgent basis.

It should be understood that the analog filter setting applies to both the HI and the HIHI alarms. Therefore, the HI alarm or the HIHI alarm is transmitted by the radio 248 when the average concentration of the selected gas over the predetermined time represented by the analog filter setting exceeds either the HI alarm setting or the HIHI alarm setting. The analog filter setting would also apply to the gas dead band determination.

By again pressing the right arrow indicia 392, the Site Address and Master Address appear at the window 232. Each gas monitor station has a unique Site Address which is coordinated with the controller at the master station 18.

By again pressing the right arrow indicia 382, an Alarm Address indication and a Set Pole Timer indicia appear at the window 232. The Alarm Address data is input to the microprocessor to indicate the location of Alarm Sites where transmission from the radio 248 at the gas monitor station 14 is to result in an alarm.

The Set Pole Timer data is entered into the microprocessor 280 by actuating the keyboard 206. The Set Pole Timer data corresponds to a maximum predetermined length of time which may elapse between radio transmissions. Thus, when a radio transmission is made, the Set Pole Timer data indicates the maximum length of time which will pass before a next radio transmission.

For example, if the Set Pole Timer data results in the microprocessor 280 being set to have a transmission every thirty minutes, the microprocessor will initiate a transmission from the radio 248 to the master station 18 after thirty minutes has elapsed from the last previous communication with the master station. This enables the master station to check to be certain that the gas monitor station 14 is functioning normally. The master station is set to report a communication failure alarm if there is no communication from a gas monitor station after a time period which is longer than the Set Pole Timer period has elapsed. In the previous example, the Set Pole Timer period was set for thirty minutes. The master station may initiate a communication failure alarm if forty-five minutes elapses between communications from a particular gas monitor station.

By again pressing the right arrow key 382, the setting for RF Diagnostics and Line Rejection appear at the window 232. The RF Diagnostics allow an individual to transmit a three second radio signal which is long enough to be displayed on a watt meter for radio/antenna integrity. The RF Diagnostics also allows an individual to send a message to the master station to verify a radio link with the master station. The Line Rejection is set to either 50 or 60 hertz power.

The CLR indicia on the keypad 206 is manually depressed to exit from the keypad after all of the desired data has been input to the microprocessor 280. All of the data which has been entered into the microprocessor by actuation of the keypad 206 is stored in the EEPROM 284 when the microprocessor 280 is shut down.

When the microprocessor 280 initiates operation of the radio 248 to transmit to the master station, the power requirements for the radio increase substantially. When the radio 248 is in a standby mode, that is, when the radio is not transmitting, the radio 248 requires a relatively small amount of current. Thus, when the radio is in a standby mode it uses less than 50 milliamps. When the radio 248 changes from the standby mode to the transmit mode, the radio uses more than 100 milliamps of current. When the radio 248 is in the transmit mode, it may use 1,000 milliamps of current. Since the radio 248 will be in a standby mode for a large majority of the time, the radio will draw a relatively small amount of current from the battery 260 and thereby tend to promote the operating life of the battery. Current drain on battery is also reduced by shutting down (de-powering) the microprocessor 280 when it is not in use.

After the gas monitor station 14 has been used for a substantial period of time, it is contemplated that it may be desired to check the sensor 38 to determine whether or not the sensor needs to be replaced. To check the sensor 38, the microprocessor 280 effects the application of a predetermined voltage to leads in the sensor cable 274. Application of this voltage to the sensor 38 results in the transmission of a different current output from the sensor back to the microprocessor 280. If the sensor 38 has not degraded and does not require replacement, the current transmitted from the sensor 38 back to the microprocessor will be a first function of the voltage which is transmitted from the microprocessor to the sensor. However, if the sensor 38 has degraded to an extent that it requires replacement, the current transmitted from the sensor 38 to the microprocessor will be a different function of the initial voltage applied to the sensor by the microprocessor.

There are a substantial number of features associated with the gas monitor station 14. It is contemplated that each of these features could be used separately or together with other features. It is contemplated that various combinations of the features disclosed herein will be used in association with other known features which are not described herein.

The invention has been described with reference to the preferred embodiment. Obviously, modifications and alterations will occur to others upon a reading and understanding of the specification. For instance, the current invention may be used to monitor for other than toxic gases and at other than chemical processing plants. And, applicant anticipates that the system will comprise other than four monitors and/or four configuration means. It is intended by applicant to include all such modifications and alterations.

Having described the invention, the following is claimed:

1. A method of monitoring for a selected gas from a potential source of the selected gas, said method comprising the steps of providing a plurality of gas monitor stations at locations spaced from the potential source of the selected gas, operating data entry apparatus disposed at each of the gas monitor stations, said step of operating data entry apparatus at each of the gas monitor stations includes entering data at each of the gas monitor stations relating to a predetermined magnitude of variation in concentration of the selected gas, sensing atmosphere adjacent to each of the gas monitor stations, and transmitting a radio signal from any one of the gas monitor stations to a master station in response to sensing of a variation in concentration of the selected gas greater than the predetermined magnitude.

2. A method as set forth in claim 1 further including the steps of determining at each of the gas monitor stations the length of time which has elapsed since transmission of a radio signal, and transmitting a radio signal from any one of the gas monitor stations to the master station upon determining that a predetermined period of time has elapsed since transmission of a radio signal from the one gas monitor station.

3. A method as set forth in claim 1 wherein said step of operating data entry apparatus at each of the gas monitor stations includes entering data relating to an average permissible magnitude of concentration of the selected gas over a predetermined period of time at each of the gas monitor stations, and transmitting a radio signal from any one of the gas monitor stations to the master station in response to sensing of an average concentration of the selected gas greater than the permissible magnitude.

4. A method as set forth in claim 1 further including the step of eliminating the effect of transient variations in the concentration of the selected gas in the atmosphere adjacent to the gas monitor stations by averaging the sensed magnitude of the selected gas over a period of time of thirty seconds or less.

5. A method as set forth in claim 1 wherein each gas monitor station includes a plurality of switches, said step of operating data entry apparatus includes manually actuating switches disposed at each of the gas monitor stations.

6. A method as set forth in claim 1 wherein a radio at each gas monitor station utilizes electrical energy at a first rate when the radio is in a transmit mode and is transmitting to the master station and utilizes electrical energy at a second rate which is less than the first rate when the radio is in a standby mode, said method further includes maintaining the radio at each of the gas monitor stations in the standby mode except when the radio is transmitting.

7. A method as set forth in claim 1 wherein each of the gas monitor stations includes a display panel, said step of operating data entry apparatus at each of the gas monitor stations includes viewing the display panel at each of the gas monitor stations and entering data in accordance with indicia displayed at the display panel.

8. A method as set forth in claim 1 wherein the data entry apparatus at each of the gas monitor stations includes an exposed keypad, said step of operating data entry apparatus includes manually actuating the exposed keypad.

9. A method as set forth in claim 1 wherein said step of entering data at each of the gas monitor stations includes entering data relating to a moving average gas concentration over a predetermined length of time, said method further includes determining when the moving average of sensed concentration over a predetermined length of time of the selected gas in the atmosphere adjacent to one of the monitor stations exceeds a predetermined magnitude, and transmitting a radio signal from the radio at the one gas monitor station to the master station in response to a determination that the moving average concentration of the selected gas over the predetermined length of time exceeds the predetermined magnitude.

10. A method as set forth in claim 1 further including the steps of transmitting a predetermined input voltage to a sensor at each of the gas monitor stations, transmitting an output voltage from the sensor at each of the gas monitor stations, and determining if the sensor at any one of the gas monitor stations should be replaced as a function of the magnitude of the output voltage.

11. A method of monitoring for a selected gas from a potential source of the selected gas, said method comprising the steps of providing a plurality of gas monitor stations at locations spaced from the potential source of the selected gas, sensing atmosphere adjacent to each of the gas monitor stations, determining when an average permissible magnitude of concentration of the selected gas has been exceeded for a predetermined period of time in the atmosphere adjacent to any one of the plurality of gas monitor stations, and transmitting a radio signal from any one of the gas monitor stations to a master station in response to determining that the average permissible magnitude of concentration of the selected gas has been exceeded for the predetermined period of time in the atmosphere adjacent to the one gas monitor station.

12. A method as set forth in claim 11 further including the step of determining when the concentration of the selected gas in the atmosphere adjacent to any one of the gas monitor stations has changed by more than a predetermined amount and transmitting a radio signal from the one gas monitor station to the master station in response to a determination that the concentration of the selected gas in the atmosphere adjacent to the one gas monitor station has changed by more than the predetermined amount.

13. A method as set forth in claim 11 further including the steps of determining at each of the gas monitor stations the length of time which has elapsed since transmission of a radio signal and transmitting a radio signal from any one of the gas monitor stations to the master station upon determining that a predetermined length of time has elapsed since transmission of a radio signal from the one gas monitor station.

14. A method as set forth in claim 13 further including the step of determining at the master station when the length of time which has elapsed since transmission of a radio signal from any one of the gas monitor stations has exceeded a length of time which is longer than the predetermined length of time and providing an alarm signal at the master station in response to a determination that the length of time which has elapsed since transmission of a radio signal from any one of the gas monitor stations has exceeded the length of time which is longer than the predetermined length of time.

15. A method as set forth in claim 11 further including the steps of transmitting a predetermined input voltage to a sensor at a gas monitor stations, transmitting from the sensor an output voltage which is a function of the input voltage and the condition of the sensor, and determining if the sensor at a one of the gas monitor stations should be replaced as a function of the output voltage from the sensor.

16. A method of monitoring for a selected gas from a potential source of the selected gas, said method comprising the steps of providing a plurality of gas monitor stations at locations spaced from the potential source of the selected gas, determining at each of the gas monitor stations when a first predetermined period of time has elapsed since a radio signal was sent from the gas monitor station to a master station, transmitting a first radio signal from each of the gas monitor stations to the master station whenever the first predetermined period of time elapses after transmission of a radio signal from the gas monitor station to the master station, providing a first alarm signal at the master station in response to a failure of any one of the gas monitor stations to send the first radio signal for more than a second predetermined period of time which is greater than the first predetermined period of time, sensing atmosphere adjacent to each of the gas monitor stations, transmitting a second radio signal from a gas monitor station to the master station when the sensed concentration of the selected gas exceeds a predetermined concentration, and providing a second alarm signal at the master station in response to the second radio signal from any one of the gas monitor stations.

17. A method as set forth in claim 16 further including the step of operating data entry apparatus at each of the gas monitor stations, said step of operating data entry apparatus at each of the gas monitor stations includes entering data at each of the gas monitor stations relating to the magnitude of the predetermined concentration of the selected gas at which the second radio signal is to be sent to the master station.

18. A method as set forth in claim 17 wherein each of the monitor stations includes a display panel and a plurality of switches, said step of operating data entry apparatus at each of the monitor stations includes viewing indicia on the display panel and effecting actuation of switches of the plurality of switches as a function of indicia on the display panel.

19. A method as set forth in claim 16 wherein a radio at each gas monitor station utilizes electrical energy at a first rate when the radio is in a transmit mode and is transmitting to the master station and utilizes electrical energy at a second rate which is less than the first rate when the radio is in a standby mode, said method further includes maintaining the radio at each of the gas monitor stations in the standby mode except when the radio is transmitting.

20. A method as set forth in claim 19 wherein each of the gas monitor stations includes a battery, said method further includes the steps of supplying electrical energy to the radio at each of the gas monitor stations from the battery at each gas monitor stations, sensing when the battery at each of the gas monitor stations contains less than a predetermined quantity of electrical energy, and transmitting a third radio signal from any one of the gas monitor stations to the master station in response to sensing that the battery contains less than the predetermined quantity of electrical energy.

21. A method as set forth in claim 20 wherein a radio at each gas monitor station utilizes electrical energy at a first rate when the radio is in a transmit mode and is transmitting to the master station an utilizes electrical energy at a second rate which is less than the first rate when the radio is in a standby mode, said method further includes maintaining the radio at each of the gas monitor stations in the standby mode except when the radio is transmitting.

22. A method as set forth in claim 16 further including the steps of transmitting a predetermined input voltage to a sensor at each of the gas monitor stations, transmitting an output voltage from the sensor at each of the gas monitor stations, and determining if the sensor at any one of the gas monitor stations should be replaced as a function of the output voltage.

23. A method of monitoring for a selected gas from a potential source of the selected gas, said method comprising the steps of providing a plurality of gas monitor stations at locations spaced from the potential source of the selected gas, sensing atmosphere adjacent to each of the gas monitor stations to determine concentration of the selected gas in the atmosphere adjacent to each of the gas monitor stations, determining when a moving average of sensed gas concentration of the selected gas over a predetermined length of time at one of the gas monitor stations exceeds a predetermined magnitude, and transmitting a radio signal from a radio at the one gas monitor station to a master station in response to a determination that the moving average of gas concentration over a predetermined length of time exceeds the predetermined magnitude.

24. A method as set forth in claim 23 further including the steps of determining at each of the gas monitor stations when a predetermined period of time has elapsed since a radio signal was sent from the gas monitor station to a master station, transmitting a radio signal from each one of the gas monitor stations to the master station whenever the predetermined period of time elapses after transmission of a radio signal from the one gas monitor station to the master station.

25. A method as set forth in claim 23 further including the step of sequentially operating data entry apparatus at each of the gas monitor stations, said step of operating data entry apparatus at each of the gas monitor stations includes sequentially entering data at each of the gas monitor stations indicative of the predetermined magnitude of the moving average of sensed gas concentration over a predetermined length of time.

26. A method as set forth in claim 25 wherein step of operating data entry apparatus at each of the gas monitor stations includes entering data at each of the gas monitor stations indicative of the duration of the predetermined length of time during which the concentration of the selected gas is to be sensed to determine the moving average of sensed concentration of the selected gas.

27. A method of monitoring for a selected gas from a potential source of the selected gas, said method comprising the steps of providing a plurality of gas monitor stations at locations spaced from the potential source of the selected gas, calibrating a sensor at one of the gas monitor stations, said step of calibrating a sensor at one of the gas monitor stations includes exposing the sensor at the one gas monitor station to gas containing a known concentration of the selected gas, transmitting data corresponding to the sensed concentration of the selected gas from the sensor at the one gas monitor station when the sensor is exposed to the gas containing a known concentration of the selected gas to a microprocessor in a control assembly at the one gas monitor station, and adjusting the control assembly at the one gas monitor station to provide an output indicative of the known concentration of the selected gas, thereafter, sensing the atmosphere adjacent to the one gas monitor station with the sensor at the one gas monitor station, transmitting data corresponding to the sensed concentration of the selected gas in the atmosphere adjacent to the one gas monitor station from the sensor at the one gas monitor station to the microprocessor in the control assembly at the one gas monitor station, transmitting a signal from the microprocessor in the control assembly at the one gas monitor station to a radio at the one gas monitor station in response to transmission to the microprocessor in the control assembly at the one gas monitor station from the sensor at the one gas monitor station of data corresponding to the predetermined concentration of the selected gas, and initiating transmission with the radio at the one gas monitor station to a master station in response to the signal transmitted from the microprocessor to the radio.

28. A method as set forth in claim 27 wherein said step of adjusting the control assembly at the one gas monitor station to provide an output indicative of the known concentration of the selected gas includes inputting of data to the microprocessor in the control assembly at the one gas monitor station, said step of inputting data includes operating data entry apparatus at the one gas monitor station.

29. A method as set forth in claim 27 wherein said step of transmitting data corresponding to the concentration of the selected gas sensed by the sensor at the one gas monitor station when the sensor is exposed to the gas containing a known concentration of the selected gas to the microprocessor in the control assembly at the one gas monitor station is performed while the sensor at the one gas monitor station is exposed to the gas containing a known concentration of the selected gas.

30. A method as set forth in claim 27 wherein said step of sensing atmosphere adjacent to the one gas monitor station is performed with the gas containing a known concentration of the selected gas isolated from the sensor at the one gas monitor station.

31. A method as set forth in claim 27 further including the step of inputting to the microprocessor in the control assembly at the one gas monitor station data corresponding to a predetermined change in the concentration of the selected gas in the atmosphere adjacent to the one gas monitor station, transmitting a signal from the microprocessor in the control assembly at the one gas monitor station to the radio at the one gas monitor station in response to transmission to the microprocessor in the control assembly at the one gas monitor station from the sensor at the one gas monitor station of data corresponding to the predetermined change in the concentration of the selected gas, and initiating transmission with the radio at the one gas monitor station to the master station in response to the signal which is transmitted from the microprocessor in the control assembly at the one gas monitor station to the radio.

32. A method as set forth in claim 27 wherein said step of adjusting the control assembly at the one gas monitor station to provide an output signal indicative of the known concentration of the selected gas includes transmitting data to the microprocessor in the control assembly at the one gas monitor station.

33. A method as set forth in claim 32 wherein said step of transmitting data to the microprocessor includes operating the data entry apparatus at the one gas monitor station to transmit data to the microprocessor.

34. A method as set forth in claim 27 wherein said step of adjusting the control assembly at the one gas monitor station to provide an output signal indicative of the known concentration of the selected gas includes the step of manually actuating a plurality of switches in a keypad at the one gas monitor station.

35. A method as set forth in claim 27 further including the steps of calibrating a sensor at each of the gas monitor stations other than the one gas monitor station by a method which includes the steps previously set forth for calibrating the sensor at the one gas monitor station.

36. A method as set forth in claim 27 further including the steps of inputting to the microprocessor in the control assembly at the one gas monitor station data corresponding to a predetermined period of time, transmitting a signal from the microprocessor in the control assembly at the one gas monitor station to the radio at the one gas monitor station in response to elapse of the predetermined period of time since transmission of a radio signal from the one gas monitor station to the master station, and initiating transmission with the radio at the one gas monitor station to the master station in response to the signal which is transmitted from the microprocessor in the control assembly at the one gas monitor station in response to elapse of the predetermined period of time since transmission of a radio signal from the one gas monitor station to the master station.

37. A method as set forth in claim 27 further including the steps of inputting to the microprocessor in the control assembly at the one gas monitor station data corresponding to an average permissible magnitude of concentration of the selected gas for a predetermined period of time in the atmosphere adjacent to the one gas monitor station, determining when the average permissible magnitude of the selected gas has been exceeded for the predetermined period of time in the atmosphere adjacent to the one gas monitor station, transmitting a signal from the microprocessor in the control assembly at the one gas monitor station to the radio at the one gas monitor station in response to a determination that the average permissible magnitude of the selected gas has been exceeded for the predetermined period of time in the atmosphere adjacent to the one gas monitor station, and initiating transmission with the radio at the one gas monitor station to the master station in response to the signal which is transmitted from the microprocessor in the control assembly at the one gas monitor station in response to a determination that the average permissible magnitude of the selected gas has been exceeded from the predetermined period of time in the atmosphere adjacent to the one gas monitor station.

38. A method as set forth in claim 27 further including the steps of transmitting a predetermined voltage from the control assembly at the one gas monitor station to the sensor at the one gas monitor station, transmitting an output voltage from the sensor at the one gas monitor station to the control assembly at the one gas monitor station, and determining if the sensor at the one gas monitor station should be replaced as a function of the magnitude of the output voltage.

39. A method as set forth in claim 27 wherein the radio at the one gas monitor station utilizes electrical energy at a first rate when the radio is in a transmit mode and is transmitting to the master station and utilizes electrical energy at a second rate which is less than the first rate when the radio is in a standby mode, said method further includes maintaining the radio at the one gas monitor station in the standby mode except when the radio is transmitting.

40. A method of monitoring for a selected gas from a potential source of the selected gas, said method comprising the steps of providing a plurality of gas monitor stations at locations spaced from the potential source of the selected gas, inputting data to a microprocessor in a control assembly at a first gas monitor station of the plurality of gas monitor stations, said step of inputting data includes inputting data corresponding to a predetermined concentration of the selected gas in the atmosphere adjacent to the first gas monitor station and inputting data corresponding to a predetermined magnitude of variation in the concentration of the selected gas, said step of inputting data to the microprocessor in the control assembly at the first gas monitor station includes actuating a plurality of switches in the control assembly at the first gas monitor station to input the data and displaying data corresponding to the data which is input to the microprocessor in the control assembly at the first gas monitor station by actuation of the switches to enable the data to be visually reviewed by an individual who is inputting the data at the first gas monitor station, thereafter, sensing the atmosphere adjacent to the first gas monitor station with a sensor assembly at the first gas monitor station, transmitting data corresponding to the sensed concentration of the selected gas in the atmosphere adjacent to the first gas monitor station from the sensor assembly at the first gas monitor station to the microprocessor in the control assembly at the first gas monitor station, transmitting a signal from the microprocessor in the control assembly at the first gas monitor station to a radio at the first gas monitor station in response to transmission to the microprocessor in the control assembly at the first gas monitor station from the sensor assembly at the first gas monitor station of data indicative of either the predetermined concentration of the selected gas in the atmosphere adjacent to the first gas monitor station or of the predetermined variation in the concentration of the selected gas in the atmosphere adjacent to the first gas monitor station, and initiating transmission with the radio at the first gas monitor station to a master station in response to the signal transmitted from the microprocessor to the radio.

41. A method as set forth in claim 40 wherein said step of actuating a plurality of switches in the control assembly at the first gas monitor station includes manually actuating an exposed keypad mounted on an outer side of a housing at the first gas monitor station, said step of displaying data corresponding to the data which is input to the microprocessor in the control assembly at the first gas monitor station includes displaying the data on a control panel which is disposed within the housing at the first gas monitor station and is visible through a window on the same outer side of the housing as on which the keypad is mounted.

42. A method as set forth in claim 40 wherein said step of inputting data to a microprocessor in the control assembly at the first gas monitor station includes inputting data corresponding to a predetermined magnitude of battery voltage to the microprocessor at the first gas monitor station, said method further includes transmitting a signal corresponding to battery voltage from a battery at the first gas monitor station to the microprocessor in the control assembly at the first gas monitor station, transmitting a low battery voltage signal from the microprocessor in the control assembly at the first gas monitor station to the radio at the first gas monitor station in response to transmission from the battery to the microprocessor of a signal corresponding to a battery voltage which is less than the predetermined magnitude of battery voltage, and initiating transmission with the radio at the first gas monitor station to the master station in response to the low battery voltage signal transmitted from the microprocessor to the radio.

43. A method as set forth in claim 40 wherein said step of inputting data to the microprocessor in the control assembly at the first gas monitor station includes inputting data corresponding to a predetermined period of time over which the sensed concentration of the selected gas in the atmosphere adjacent to the first gas monitor station is to be averaged to eliminate the effect of short duration variations in the concentration of the selected gas in the atmosphere adjacent to the first gas monitor station, said step of transmitting a signal from the microprocessor in the control assembly at the first gas monitor station to the radio at the first gas monitor station in response to transmission to the microprocessor in the control assembly at the first gas monitor station from the sensor assembly at the first gas monitor station of data indicative of the predetermined concentration of the selected gas in the atmosphere adjacent to the first gas monitor station being performed when the average sensed concentration of the selected gas over the predetermined period of time in the atmosphere adjacent to the first gas monitor station is at least the predetermined concentration of the selected gas.

44. A method as set forth in claim 40 wherein said step of inputting data to the microprocessor in the control assembly at the first gas monitor station includes inputting data relating to a moving average gas concentration over a predetermined length of time, said method further includes determining when the moving average of sensed concentration over a predetermined length of time of the selected gas in the atmosphere adjacent to the first gas monitor station exceeds a predetermined magnitude, transmitting a short term exposure limit signal from the microprocessor in the control assembly at the first gas monitor station to the radio at the first gas monitor station in response to a determination that the moving average gas concentration over a predetermined length of time of the selected gas exceeds the predetermined magnitude, and initiating transmission with the radio at the first gas monitor station to the master station in response to the short term exposure limit signal transmitted from the microprocessor to the radio.

45. A method of monitoring for a selected gas from a potential source of the selected gas, said method comprising the steps of providing a plurality of gas monitor stations at locations spaced from the potential source of the selected gas with each of the gas monitor stations having a gas sensor assembly, a control assembly, a radio, a keypad, and a display, manually actuating the keypad at each of the gas monitor stations to enter data corresponding to a predetermined concentration of the selected gas into the control assembly at each of the gas monitor stations, viewing the display at each of the gas monitor stations to review the data entered into the control assembly at each of the gas monitor stations as a result of actuating the key pad at each of the gas monitor stations, sensing the atmosphere adjacent to each of the gas monitor stations with the sensor assemblies, transmitting data indicative of the sensed concentration of the selected gas from the sensor assembly at each of the gas monitor stations to the control assembly at each of the gas monitor stations, and initiating transmission with the radio at any one of the gas monitor stations to a master station when the sensed concentration of the selected gas in the atmosphere adjacent to the one gas monitor station is at least as great as the predetermined concentration of the selected gas.

46. A method as set forth in claim 45 wherein each of the gas monitor stations includes a housing which is operable between a closed condition blocking access to the control assembly at each of the gas monitor stations and an open condition providing access to the control assembly at each of the gas monitor stations, said step of manually actuating the keypad at each of the gas monitor stations being performed with the housing in the closed condition and with the keypad exposed to the atmosphere adjacent to each of the gas monitor stations.

47. A method as set forth in claim 45 wherein further including the step of calibrating the sensor at each of the gas monitor stations, said step of calibrating the sensor at each of the gas monitor stations includes exposing the sensor at each of the gas monitor stations to a container of gas containing a known concentration of the selected gas, viewing data displayed at the display at each of the gas monitor stations and corresponding to the sensed concentration of the selected gas in the container of gas, and manually actuating the keypad at each of the gas monitor stations to adjust the displayed data to correspond to the known concentration of the selected gas in the container of gas.

48. A method as set forth in claim 45 further including the steps of manually actuating the keypad at each of the gas monitor stations to effect application of a predetermined voltage to the sensor assembly at each of the gas monitor stations, viewing displayed data corresponding to voltage transmitted from the sensor assembly at each of the gas monitor stations, and determining if the sensor assembly at any one of the gas monitor stations should be replaced as a function of the displayed data.

49. A method as set forth in claim 45 further including the steps of manually actuating the keypad at each of the gas monitor stations to enter data corresponding to a predetermined variation in concentration of the selected gas into the control assembly at each of the gas monitor stations, viewing the display at each of the gas monitor stations to review the data entered into the control assembly and corresponding to a predetermined variation in concentration of the selected gas, and initiating transmission with the radio at each of the gas monitor stations to the master station when the sensed concentration of the selected gas in the atmosphere adjacent to each of the gas monitor stations changes by an amount which is at least as great as the predetermined variation.

50. A method as set forth in claim 45 further including the steps of manually actuating the keypad at each of the gas monitor stations to enter data corresponding to a predetermined maximum length of time between radio transmissions from the gas monitor station to the master station into the control assembly at each of the gas monitor stations, viewing the display at each of the gas monitor stations to review the data entered into the control assembly and corresponding to the predetermined maximum length of time between radio transmissions from the gas monitor stations to the master station, determining at each of the gas monitor stations the length of time which has elapsed since the last radio transmission to the master station, and initiating transmission with the radio at each of the gas monitor stations to the master station upon determining that the predetermined maximum length of time has elapsed since the last radio transmission to the master station.

51. A method as set forth in claim 45 further including the step of manually actuating the keypad at each of the gas monitor stations to enter data corresponding to an average predetermined concentration of the selected gas over a predetermined period of time into the control assembly at each of the gas monitor stations, viewing the display at each of the gas monitor stations to review the data entered into the control assembly and corresponding to the average predetermined concentration of the selected gas over a predetermined time, and transmitting data corresponding to the average predetermined concentration of the selected gas to the master station upon performance of said step of initiating transmission with the radio at each of the gas monitor stations to the master station.

52. A method as set forth in claim 45 further including the step of eliminating the effect of transient variations in the concentration of the selected gas in the atmosphere adjacent to the gas monitor stations by averaging the sensed magnitude of the sensed gas over a period of time of thirty seconds or less.

53. A method as set forth in claim 45 including the steps of manually actuating the keypad at each of the gas monitor stations to enter data corresponding to a moving average gas concentration over a predetermined length of time into the control assembly at each of the gas monitor stations, viewing the display at each of the gas monitor stations to review the data entered into the control assembly and corresponding to the concentration over a predetermined length of time, determining at each of the gas monitor stations when the moving average sensed concentration over a predetermined length of time of the selected gas in the atmosphere exceeds a predetermined magnitude, and initiating transmission with the radio at each of the gas monitor stations to the master station upon determining that the moving average concentration over the predetermined length of time of the selected gas in the atmosphere adjacent to one of the gas monitor stations exceeds the predetermined magnitude.

54. A method as set forth in claim 45 including the steps of manually actuating the keypad at each of the gas monitor stations to enter data corresponding to a predetermined magnitude of battery voltage into the control assembly at each of the gas monitor stations, viewing the display at each of the gas monitor stations to review the data entered into the control assembly and corresponding to the predetermined magnitude of battery voltage, determining at each of the gas monitor stations when a battery at each of the gas monitor stations has an output voltage less than the predetermined magnitude, and initiating transmission with the radio at each of the gas monitor stations to the master station upon determining that the battery at each of the gas monitor stations has an output voltage which is less than the predetermined magnitude.

55. A method of monitoring for a selected gas from a potential source of the selected gas, said method comprising the steps of providing a plurality of gas monitor stations at selected locations spaced from the potential source of the gas with each of the gas monitor stations having a gas sensor assembly and a radio, sensing the atmosphere adjacent to each of the gas monitor stations with the sensor assemblies, initiating transmission with the radio at any one of the gas monitor stations to a master station when the sensed concentration of the selected gas in the atmosphere adjacent to the one gas monitor station is at least as great as a predetermined concentration of the selected gas, transmitting a predetermined input voltage to the sensor assembly at each of the gas monitor stations, transmitting an output voltage from the sensor assembly at each of the gas monitor stations, and determining if the sensor assembly at any one of the gas monitor stations should be replaced as a function of the magnitude of the output voltage.

56. A method as set forth in claim 55 wherein each of the gas monitor stations has a battery and a control assembly connected with the battery, said step of transmitting predetermined input voltage to the sensor assembly at each of the gas monitor stations includes transmitting the predetermined input voltage from the control assembly at each of the gas monitor stations to the sensor assembly at each of the gas monitor stations, said step of transmitting an output voltage from the sensor assembly at each of the gas monitor stations includes transmitting the output voltage from the sensor assembly at each of the gas monitor stations to the control apparatus at each of the gas monitor stations.

57. A method as set forth in claim 55 further including the step of calibrating the sensor assembly at each of the gas monitor stations, said step of calibrating the sensor assembly at each of the gas monitor stations includes exposing the sensor assembly at one of the gas monitor stations to gas in a container of gas containing a known concentration of the selected gas, transmitting data corresponding to the concentration of the selected gas sensed by the sensor assembly at the one gas monitor assembly to a control assembly in the gas monitor station, and adjusting the control assembly at the one gas monitor station to provide an output indicative of the known concentration of the selected gas in the container.

58. A method of monitoring for a selected gas from a potential source of the selected gas, said method comprising the steps of providing a plurality of gas monitor stations at locations spaced from the potential source of the selected gas, inputting data to a microprocessor in a control assembly at a first gas monitor station of the plurality of gas monitor stations, said step of inputting data includes inputting data corresponding to a predetermined concentration of the selected gas, said step of inputting data to the microprocessor in the control assembly at the first gas monitor station includes actuating data entry apparatus which forms part of the control assembly at the first gas monitor station to input the data and displaying data corresponding to the data which is input to the microprocessor in the control assembly at the first gas monitor station by actuation of the data entry apparatus in the control assembly at the fist gas monitor station to enable the data to be visually reviewed by an individual who is inputting the data at the first gas monitor station, said step of displaying data corresponding to the data which is input to the microprocessor includes displaying the data at a display which forms part of the control assembly at the first gas monitor station, thereafter, sensing the atmosphere adjacent to the first gas monitor station with a sensor assembly at the first gas monitor station, transmitting data corresponding to the sensed concentration of the selected gas in the atmosphere adjacent to the first gas monitor station from the sensor assembly at the first gas monitor station to the microprocessor in the control assembly at the first gas monitor station, transmitting a signal from the microprocessor in the control assembly at the first gas monitor station to a radio at the first gas monitor station in response to transmission to the microprocessor in the control assembly at the first gas monitor station from the sensor assembly at the first gas monitor station of data indicative of the predetermined concentration of the selected gas in the atmosphere adjacent to the first gas monitor station, and initiating transmission with the radio at the first gas monitor station to a master station in response to the signal transmitted from the microprocessor to the radio.

59. A method as set forth in claim 58 wherein said step of actuating data entry apparatus in the control assembly at the first gas monitor station includes manually actuating an exposed keypad mounted on an outer side of a housing at the first gas monitor station, said step of displaying data corresponding to the data which is input to the microprocessor in the control assembly at the first gas monitor station includes displaying the data on a control panel which is disposed within the housing at the first gas monitor station and is visible through a window on the same outer side of the housing as on which the keypad is mounted.

60. A method as set forth in claim 58 wherein said step of inputting data to a microprocessor in the control assembly at the first gas monitor station includes inputting data corresponding to a predetermined magnitude of battery voltage to the microprocessor at the first gas monitor station, said method further includes transmitting a signal corresponding to battery voltage from a battery at the first gas monitor station to the microprocessor in the control assembly at the first gas monitor station, transmitting a low battery voltage signal from the microprocessor in the control assembly at the first gas monitor station to the radio at the first gas monitor station in response to transmission from the battery to the microprocessor of a signal corresponding to a battery voltage which is less than the predetermined magnitude of battery voltage, and initiating transmission with the radio at the first gas monitor station to the master station in response to the low battery voltage signal transmitted from the microprocessor to the radio.

61. A method as set forth in claim 58 wherein said step of inputting data to the microprocessor in the control assembly at the first gas monitor station includes inputting data corresponding to a predetermined period of time over which the sensed concentration of the selected gas in the atmosphere adjacent to the first gas monitor station is to be averaged to eliminate the effect of short duration variations in the concentration of the selected gas in the atmosphere adjacent to the first gas monitor station, said step of transmitting a signal from the microprocessor in the control assembly at the first gas monitor station to the radio at the first gas monitor station in response to transmission to the microprocessor in the control assembly at the first gas monitor station from the sensor assembly at the first gas monitor station of data indicative of the predetermined concentration of the selected gas in the atmosphere adjacent to the first gas monitor station being performed when the average sensed concentration of the selected gas over the predetermined period of time in the atmosphere adjacent to the first gas monitor station is at least the predetermined concentration of the selected gas.

62. A method as set forth in claim 58 wherein said step of inputting data to the microprocessor in the control assembly at the first gas monitor station includes inputting data relating to a moving average gas concentration over a predetermined length of time, said method further includes determining when the moving average of sensed concentration over a predetermined length of time of the selected gas in the atmosphere adjacent to the first gas monitor station exceeds a predetermined magnitude, transmitting a short term exposure limit signal from the microprocessor in the control assembly at the first gas monitor station to the radio at the first gas monitor station in response to a determination that the moving average gas concentration over a predetermined length of time of the selected gas exceeds the predetermined magnitude, and initiating transmission with the radio at the first gas monitor station to the master station in response to the short term exposure limit signal transmitted from the microprocessor to the radio.

63. A method as set forth in claim 58 wherein said step of inputting data includes inputting data corresponding to a predetermined magnitude of variation in the concentration of the selected gas, transmitting a second signal from the microprocessor in the control assembly at the first gas monitor station to the radio at the first gas monitor station in response to transmission to the microprocessor in the control assembly at the first gas monitor station from the sensor assembly at the first gas monitor station of data indicative of the predetermined variation in the concentration of the selected gas in the atmosphere adjacent to the first gas monitor station, and initiating transmission with the radio in the first gas monitor station to the master station in response to the second signal transmitted from the microprocessor to the radio.

64. A method as set forth in claim 58 further including the steps of inputting data to a microprocessor in a second control assembly at a second gas monitor station of the plurality of gas monitor stations, said step of inputting data at a second gas monitor station includes inputting data corresponding to the predetermined concentration of the selected gas, said step of inputting data to the microprocessor in the second control assembly at the second gas monitor station includes actuating second data entry apparatus which forms part of the second control assembly at the second gas monitor station to input the data and displaying data corresponding to the data which is input to the microprocessor in the second control assembly at the second gas monitor station by actuation of the second data entry apparatus in the second control assembly at the second gas monitor station to enable the data to be visually reviewed by an individual who is inputting the data at the second gas monitor station, said step of displaying data corresponding to the data which is input to the microprocessor in the second control assembly includes displaying the data at a second display which forms part of the second control assembly at the second gas monitor station, thereafter, sensing the atmosphere adjacent to the second gas monitor station with a second sensor assembly at the second gas monitor station, transmitting data corresponding to the sensed concentration of the selected gas in the atmosphere adjacent to the second gas monitor station from the second sensor assembly at the second gas monitor station to the microprocessor in the second control assembly at the second gas monitor station, transmitting a signal from the microprocessor in the second control assembly at the second gas monitor station to a radio at the second gas monitor station in response to transmission to the microprocessor in the second control assembly at the second gas monitor station from the second sensor assembly at the second gas monitor station of data indicative of the predetermined concentration of the selected gas in the atmosphere adjacent to the second gas monitor station, and initiating transmission with the radio at the second gas monitor station to a master station in response to the signal transmitted from the microprocessor at the second gas monitor station to the radio at the second gas monitor station.

* * * * *